(12) United States Patent
Nobles et al.

(10) Patent No.: US 7,803,167 B2
(45) Date of Patent: Sep. 28, 2010

(54) HANDLE FOR SUTURING APPARATUS

(76) Inventors: Anthony A. Nobles, 8686 Tern Ave., Fountain Valley, CA (US) 92708; Steven E. Decker, 1295 N. Amelia St., Anaheim, CA (US) 93807; Hung Tran, 805 N. Taft St., Santa Ana, CA (US) 92703; Benjamin G. Brosch, 27261 Nubles, Mission Viejo, CA (US) 92692

( * ) Notice: Subject to any disclaimer, the term of this patent is extended or adjusted under 35 U.S.C. 154(b) by 1289 days.

(21) Appl. No.: 11/235,751

(22) Filed: Sep. 27, 2005

(65) Prior Publication Data

US 2006/0069397 A1 Mar. 30, 2006

Related U.S. Application Data

(60) Provisional application No. 60/613,636, filed on Sep. 27, 2004.

(51) Int. Cl.
*A61B 17/04* (2006.01)
(52) U.S. Cl. ............... 606/144; 606/147; 606/181; 606/182; 606/184; 606/185
(58) Field of Classification Search ............. 606/144, 606/148, 181–182, 184–185; 227/107, 134
See application file for complete search history.

(56) References Cited

U.S. PATENT DOCUMENTS

| | | | |
|---|---|---|---|
| 1,593,347 A * | 7/1926 | Nardi | 401/33 |
| 2,601,564 A | 6/1952 | Smith | |
| 2,741,225 A * | 4/1956 | Fink | 401/114 |
| 2,741,226 A * | 4/1956 | Dietrich et al. | 401/112 |

(Continued)

FOREIGN PATENT DOCUMENTS

EP 0 870 486 A 10/1998

(Continued)

OTHER PUBLICATIONS

Partial International Search which is Annex to the Invitation to Pay Additional Fees in counterpart International Application No. PCT/US2005/034801, dated Feb. 17, 2006.

(Continued)

*Primary Examiner*—Darwin P Erezo
*Assistant Examiner*—Son Dang
(74) *Attorney, Agent, or Firm*—Knobbe, Martens, Olson & Bear, LLP

(57) ABSTRACT

Methods and apparatus are provided for closing incisions within biological tissue. In one embodiment, a device and method are provided for suturing biological tissue, such as, for example, an organ or blood vessel. The suturing apparatus is particularly well suited for suturing an incision made in an artery, such as the femoral artery, following a catheterization procedure. The device eliminates the need to apply pressure to a patient's thigh for an extended period of time, and eliminates many of the complications and costs associated with the creation of a thrombus patch. In addition, the device comprises an improved handle portion which enables the physician to quickly and easily apply suture. The handle portion is very reliable and easy to manipulate. The suturing may be used in combination with existing catheter sheath introducers.

13 Claims, 26 Drawing Sheets

U.S. PATENT DOCUMENTS

| | | | |
|---|---|---|---|
| 2,748,748 A * | 6/1956 | Lovejoy | 401/114 |
| 2,790,422 A * | 4/1957 | Grumbach | 401/33 |
| 2,959,172 A | 11/1960 | Held | |
| 3,098,467 A * | 7/1963 | Nagele Jr | 401/33 |
| 3,107,654 A * | 10/1963 | Fehrenbach | 401/31 |
| 3,260,242 A * | 7/1966 | Liguori | 401/31 |
| 3,262,427 A * | 7/1966 | Von Arx | 401/31 |
| 3,294,068 A * | 12/1966 | Hechtle | 401/31 |
| 3,301,221 A * | 1/1967 | Von Arx | 401/31 |
| 3,989,389 A * | 11/1976 | Hashimoto et al. | 401/30 |
| 4,022,535 A * | 5/1977 | Ritter | 401/32 |
| 4,553,543 A | 11/1985 | Amarashinghe | |
| 4,841,888 A | 6/1989 | Mills et al. | |
| 4,957,498 A | 9/1990 | Caspari et al. | |
| 4,988,339 A * | 1/1991 | Vadher | 604/197 |
| 5,059,201 A | 10/1991 | Asnis | |
| 5,196,025 A * | 3/1993 | Ranalletta et al. | 606/182 |
| 5,222,508 A | 6/1993 | Contarini | |
| 5,254,126 A | 10/1993 | Filipi et al. | |
| 5,304,184 A | 4/1994 | Hathaway et al. | |
| 5,320,632 A * | 6/1994 | Heidmueller | 606/144 |
| 5,336,229 A | 8/1994 | Noda | |
| 5,364,408 A * | 11/1994 | Gordon | 606/144 |
| 5,368,601 A | 11/1994 | Sauer et al. | |
| 5,374,275 A | 12/1994 | Bradley et al. | |
| 5,383,897 A | 1/1995 | Wholey | |
| 5,387,221 A | 2/1995 | Bisgaard | |
| 5,395,383 A | 3/1995 | Adams et al. | |
| 5,403,329 A | 4/1995 | Hinchcliffe | |
| 5,417,699 A | 5/1995 | Klein et al. | |
| 5,417,700 A | 5/1995 | Egan | |
| 5,431,666 A | 7/1995 | Sauer et al. | |
| 5,458,609 A | 10/1995 | Gordon et al. | |
| 5,462,560 A * | 10/1995 | Stevens | 606/144 |
| 5,462,561 A | 10/1995 | Voda | |
| 5,470,338 A | 11/1995 | Whitfield et al. | |
| 5,474,568 A | 12/1995 | Scott | |
| 5,476,469 A | 12/1995 | Hathaway et al. | |
| 5,476,470 A | 12/1995 | Fitzgibbons, Jr. | |
| 5,496,332 A | 3/1996 | Sierra et al. | |
| 5,499,991 A | 3/1996 | Garman et al. | |
| 5,501,691 A * | 3/1996 | Goldrath | 606/148 |
| 5,507,755 A | 4/1996 | Gresl et al. | |
| 5,507,757 A | 4/1996 | Sauer et al. | |
| 5,520,702 A | 5/1996 | Sauer et al. | |
| 5,527,321 A | 6/1996 | Hinchliffe | |
| 5,527,322 A | 6/1996 | Klein et al. | |
| 5,540,704 A | 7/1996 | Gordon et al. | |
| 5,562,686 A | 10/1996 | Sauer et al. | |
| 5,562,688 A * | 10/1996 | Riza | 606/148 |
| 5,573,540 A | 11/1996 | Yoon | |
| 5,578,044 A * | 11/1996 | Gordon et al. | 606/144 |
| 5,613,974 A | 3/1997 | Andreas et al. | |
| 5,613,975 A | 3/1997 | Christy | |
| 5,632,752 A | 5/1997 | Buelna | |
| 5,662,663 A | 9/1997 | Shallman | |
| 5,662,664 A | 9/1997 | Gordon et al. | |
| 5,700,273 A * | 12/1997 | Buelna et al. | 606/148 |
| 5,713,910 A | 2/1998 | Gordon et al. | |
| 5,779,719 A | 7/1998 | Klein et al. | |
| 5,792,152 A | 8/1998 | Klein et al. | |
| 5,810,849 A | 9/1998 | Kontos | |
| 5,817,110 A | 10/1998 | Kronner | |
| 5,836,955 A * | 11/1998 | Buelna et al. | 606/148 |
| 5,836,956 A * | 11/1998 | Buelna et al. | 606/148 |
| 5,846,253 A * | 12/1998 | Buelna et al. | 606/148 |
| 5,860,990 A * | 1/1999 | Nobles et al. | 606/144 |
| 5,860,991 A | 1/1999 | Klein | |
| 5,868,762 A | 2/1999 | Cragg et al. | |
| 5,944,730 A | 8/1999 | Nobles et al. | |
| 5,954,732 A | 9/1999 | Hart et al. | |
| 5,972,005 A | 10/1999 | Stalker et al. | |
| 6,042,601 A | 3/2000 | Smith | |
| 6,048,351 A | 4/2000 | Gordon et al. | |
| 6,059,800 A | 5/2000 | Hart et al. | |
| 6,077,276 A | 6/2000 | Kontos | |
| 6,117,144 A * | 9/2000 | Nobles et al. | 606/144 |
| 6,136,010 A | 10/2000 | Modesitt et al. | |
| 6,187,026 B1 | 2/2001 | Devlin et al. | |
| 6,190,396 B1 | 2/2001 | Whitin et al. | |
| 6,245,079 B1 * | 6/2001 | Nobles et al. | 606/144 |
| 6,280,460 B1 | 8/2001 | Bolduc et al. | |
| 6,537,299 B1 | 3/2003 | Hogendijk et al. | |
| 6,551,331 B2 * | 4/2003 | Nobles et al. | 606/144 |
| 6,562,052 B2 * | 5/2003 | Nobles et al. | 606/144 |
| 6,911,034 B2 * | 6/2005 | Nobles et al. | 606/144 |
| 6,964,668 B2 * | 11/2005 | Modesitt et al. | 606/144 |
| 7,004,952 B2 * | 2/2006 | Nobles et al. | 606/144 |
| 7,090,686 B2 * | 8/2006 | Nobles et al. | 606/144 |
| 2003/0195539 A1 | 10/2003 | Attinger et al. | |
| 2004/0068273 A1 | 4/2004 | Fariss et al. | |

FOREIGN PATENT DOCUMENTS

| | | |
|---|---|---|
| EP | 0 941 698 A1 | 9/1999 |
| WO | WO 97/07745 | 3/1997 |
| WO | WO 99/25254 A | 5/1999 |

OTHER PUBLICATIONS

International Search Report for PCT/US05/034801 mailed Apr. 5, 2007 in 10 pages.

International Search Report and Written Opinion of the International Searching Authority in related Application No. PCT/US2005/034801, mailed May 22, 2006.

* cited by examiner

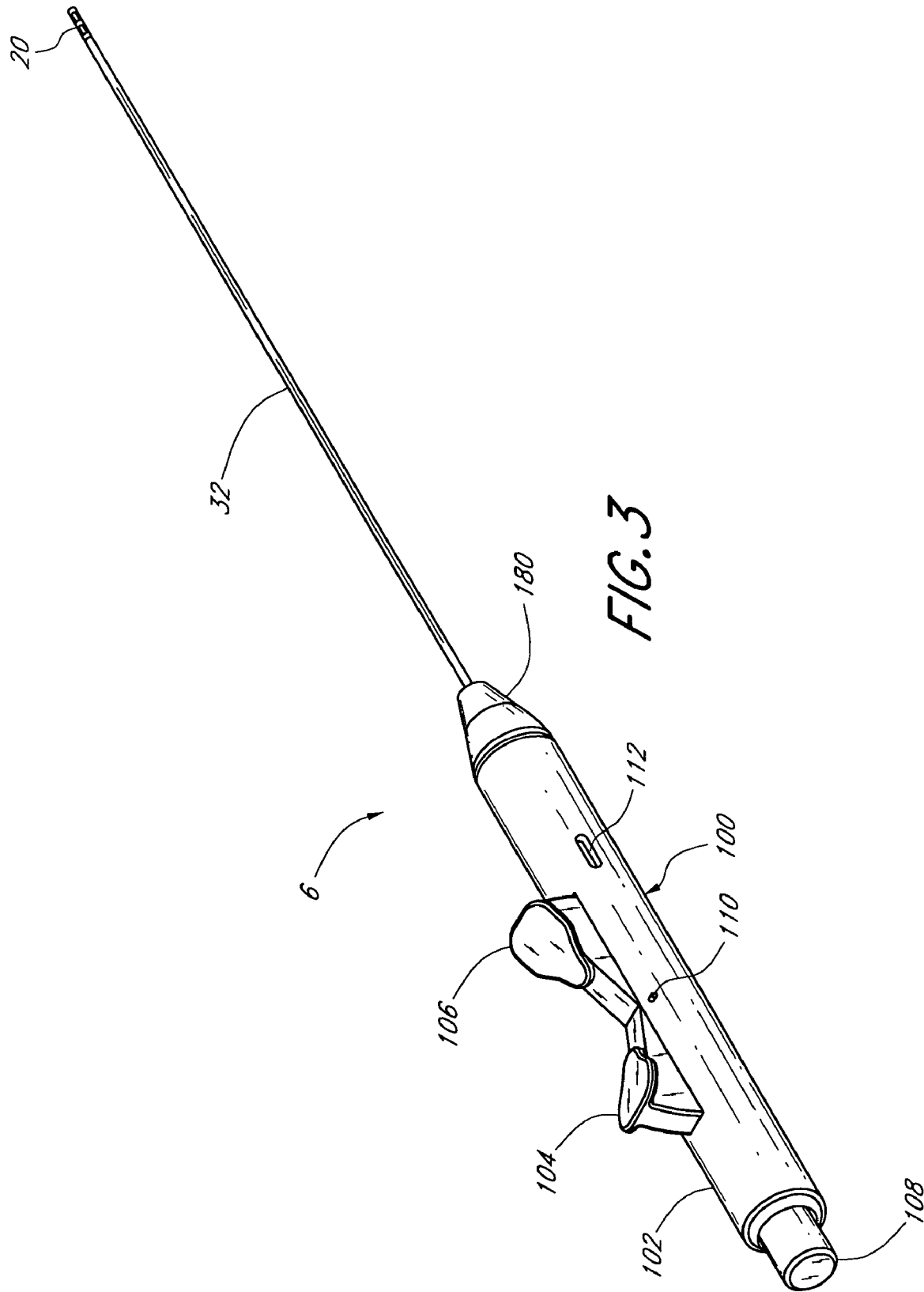

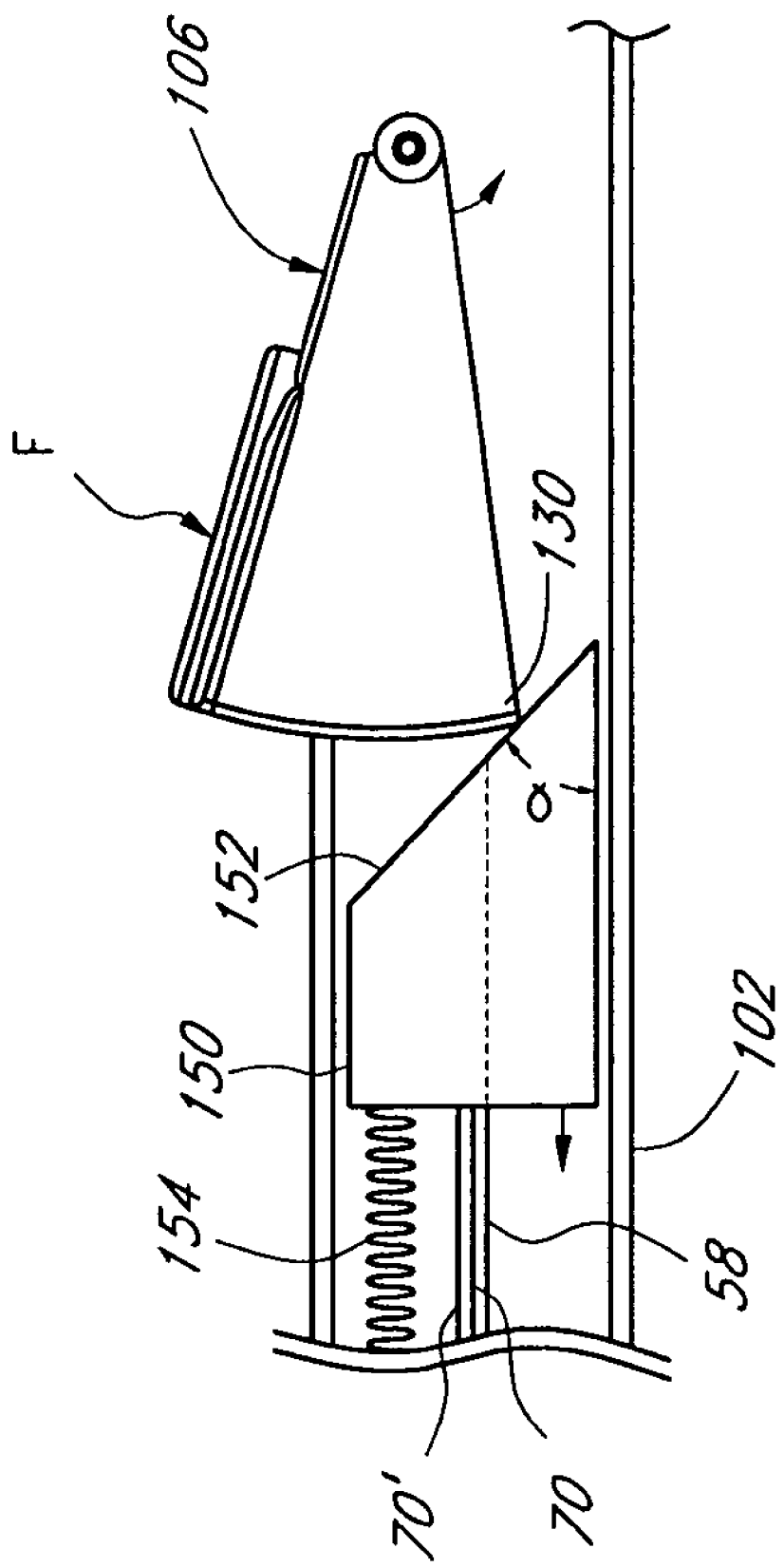

HANDLE FOR SUTURING APPARATUS

CROSS-REFERENCE TO RELATED APPLICATION

This application claims the benefit of U.S. Provisional Application No. 60/613,636, filed Sep. 27, 2004, the entirety of which is hereby incorporated by reference.

BACKGROUND OF THE INVENTION

1. Field of the Invention

The invention relates generally to a suturing apparatus. More specifically, the invention relates to a device and method for applying suture within biological tissue that may not be directly accessible to the physician.

2. Description of the Related Art

Physicians frequently use suture to close cuts, punctures, incisions and other openings in various biological tissue, such as blood vessels, of the human body.

In an arterial catheterization procedure, a relatively small percutaneous incision is made in the femoral or other artery. A catheter is inserted through the incision and directed along an arterial path to a target area, such as the heart, to perform one or more procedures, such as an angioplasty or angiogram. These procedures are intended to be relatively quick 'outpatient' procedures.

Upon completion of the catheterization procedure, the physician typically creates a 'thrombus patch' by applying direct pressure to the patient's thigh to make the blood around the incision clot. It is very important that the applied pressure does not impede the flow of blood through the femoral artery. As a result, it is commonplace for the physician to apply direct pressure by hand for the first twenty minutes after the procedure. During this time, the physician can feel the pulse to assure the artery is not occluded. Afterwards, the physician typically transfers responsibility to an assistant who then applies direct pressure using sandbags, clamps or other devices. A significant problem with this approach is that it is frequently necessary to apply the pressure for an extended period of time, such as twenty-four hours or longer.

Another problem with the thrombus patch method is that the high blood pressure in the artery can cause the thrombus patch to rupture or burst while direct pressure is being applied to the thigh or after direct pressure is removed. This requires the entire process to be reinitiated. If the patch ruptures and is not quickly restored, substantial bleeding can occur, with potentially fatal consequences. Because thrombus patches frequently burst, the patient is often kept in the hospital or catheterization lab overnight for observation. As a result, these 'out-patient' procedures become 'in-patient' procedures, simply because a thrombus patch is often unreliable and/or difficult to create. Staying in the hospital increases patient discomfort and hospital expenses, which are often disproportionate to the actual medical procedure performed.

Furthermore, if a thrombus patch cannot be adequately formed, the physician may need to anesthetize the patient and occlude the blood flow to the artery. At this point, the physician is required to make a large incision in the thigh to allow conventional suturing with a needle, suture the artery with conventional means, restore blood flow to the artery, and suture the incision in the thigh. This results in additional discomfort and expenses for the patient.

While the above problems could potentially be avoided by suturing the blood vessel immediately following the catheterization procedure, the size and location of the artery make suturing extremely difficult. More specifically, the opening in the thigh is often too small and too deep to provide enough working space for suturing the artery using conventional methods. Thus, in order to suture the vessel using conventional methods, the opening in the thigh would have to be significantly enlarged, thereby further increasing the recovery period and exposing the patient to additional discomfort, undesirable scarring, possible infection and other health risks.

SUMMARY OF THE INVENTION

Methods and devices are provided for closing incisions within biological tissue. In one embodiment, a device and method are provided for suturing biological tissue, such as, for example, an organ or blood vessel. The device is particularly well suited for suturing an incision made in an artery, such as the femoral artery, following a catheterization procedure. The device eliminates the need to apply pressure to a patient's thigh for an extended period of time, and eliminates many of the complications and costs associated with the creation of a thrombus patch. In one feature, the device comprises an improved handle portion that allows the physician to apply suture in a quick and efficient manner. The handle portion is very simple to operate, thereby reducing or eliminating the possibility of human error during use. In addition, the actuation mechanisms on the handle portion allow the physician to maintain the device in a steady position while applying suture.

In one preferred embodiment, a suturing apparatus comprises an elongate body and an arm mounted to move relative to the elongate body. The arm is formed with a suture mounting portion which mounts an end portion of a suture. The suturing apparatus further comprises a needle having a distal end, wherein the needle is mounted to move relative to the elongate body. A handle is attached to the elongate body and comprises an actuator having a camming surface and a follower having a cammed surface. The follower is connected to move the needle, wherein the camming surface and cammed surface interact in response to movement of the actuator to drive the follower to move the needle.

In one variation, the handle has a longitudinal axis, wherein at least a portion of the cammed surface is inclined about 35° or more relative to the axis. In another variation, at least a portion of the cammed surface is inclined about 40° or more relative to the axis. In another variation, at least a portion of the cammed surface is inclined at about 41° relative to the axis. In another variation, at least a portion of the cammed surface is inclined at between about 35-45° relative to the axis. In another variation, at least a portion of the cammed surface is inclined at between about 39-43° relative to the axis. In another variation, at least a portion of the cammed surface is inclined at between about 40-42° relative to the axis. In another variation, the camming surface is curved.

In another preferred embodiment, a suturing apparatus comprises an elongate body and an arm is mounted to move relative to the elongate body. The arm has a suture mounting portion which mounts an end portion of a suture. A needle having a distal end is mounted to move relative to the elongate body wherein the distal end of the needle is movable. A handle is attached to the elongate body. The handle comprises an actuator and a follower connected to move the needle by an amount equal to movement of the follower, wherein the amount of movement of the follower is visible to the user. Accordingly, the amount of movement of the needle may be monitored without directly viewing the needle.

In one variation, the handle has a housing portion comprised of a transparent material, wherein the follower is visible to the user through the transparent material. In another variation, the needle moves from a start position to a finish position in response to movement of the actuator, wherein the handle includes indicia that at least indicates the position of the follower when the needle is in the finish position. If desired, the indicia may further indicate the position of the follower when the needle is in the start position. In another preferred embodiment, a portion of one or both follower members may be visible and/or extend through the main housing, such that the amount of movement of the needle may be monitored without directly viewing the needle.

In another preferred embodiment, a suturing apparatus comprises an elongate body and an arm mounted to move relative to the elongate body. The arm is formed with a suture mounting portion which mounts an end portion of a suture. The suturing apparatus further comprises a needle having a distal end, wherein the needle is mounted to move relative to the elongate body. A handle is attached to the elongate body, the handle comprising an actuator having a camming surface and a follower having a cammed surface. The follower is connected to move the needle such that movement of the follower in a distal direction drives the needle in a distal direction and movement of the follower in a proximal direction drives the needle in a proximal direction. The follower is preferably spring biased towards a proximal direction and has a range of movement. The camming surface and cammed surface interact to drive the follower in a distal direction during at least a substantial portion of the range of movement.

In one variation, the actuator has a first finish position, wherein interaction of the cammed surface and camming surface is released in the first finish position such that the spring biasing drives the follower in a proximal direction, thereby automatically retracting the needle in a proximal direction, without retracting the actuator from the first finish position. The actuator may also have a second finish position in which the spring biasing further retracts the needle. The actuator and the follower are relatively configured such that the follower is driven in a proximal direction at a substantially faster rate upon reaching the second finish position than upon reaching the first finish position.

In another variation, the actuator has a finish position in which the needle is at a distal end of a range of movement of the needle. The spring biasing of the follower retracts the needle in a proximal direction in response to retraction of the actuator from the finish position.

In another preferred embodiment, a method of applying suture to an opening is provided. The method comprises inserting an elongate body into the opening and then extending at least one arm from the elongate body on a distal side of the opening, the at least one arm holding a suture portion. At least one needle is advanced from the elongate body from the proximal side of the opening, through tissue adjacent the opening, and into engagement with the suture portion held by the at least one arm. The needle is advanced by moving an actuator from a first position to a second position and is biased to retract to its first position. The at least one needle is then retracted in a distal to proximal direction, pulling the suture portion proximally through the opening. In one variation, the actuator is depressed to advance the needle. In another variation, the needle retracts by releasing the actuator to return to its first position. In another variation, the needle automatically retracts by further depressing the actuator. In still another variation, the needle is spring biased to return to its first position.

In yet another preferred embodiment, a method of applying suture to an opening is provided. The method comprises inserting an elongate body into the opening, the elongate body being connected to a handle having a plurality of actuators. A first actuator is depressed to extend at least one arm from a first position to a second position, the arm in its second position extending from the elongate body on a distal side of the opening, the at least one arm holding a suture portion. A second actuator is depressed to advance at least one needle from the elongate body from the proximal side of the opening, through tissue adjacent the opening, and into engagement with the suture portion held by the at least one arm. The at least one needle is retracted in a distal to proximal direction, pulling the suture portion proximally through the opening and the arm is retracted to its first position. In one variation, a third actuator is depressed to return the at least one arm from its second position to its first position. In another variation, the needle is retracted by returning the second actuator to its initial position. In yet another variation, the needle is spring biased to return to its initial position.

In yet another preferred embodiment, a method of advancing a needle comprises providing an actuator capable of being depressed and providing a follower having an angled surface, the follower being connected with the needle and the angled surface being engageable with a surface of the actuator. The actuator is depressed to advance the needle, wherein the distance moved by the needle is proportional to the angle of the angled surface.

In yet another preferred embodiment, a method of advancing a needle comprises providing a suturing device having a handle portion and an elongate body, the elongate body having a distal end portion sized for insertion through a vessel wall, the suturing device having two deployable suture arms for holding ends of a suture and two extendable needles for grabbing the ends of the suture from the arms. The elongate body is advanced through an incision in the vessel wall. A first actuator is depressed on the handle portion for deploying the suture arms within the vessel. A second actuator is depressed on the handle portion for extending the needles through the vessel wall for grabbing the ends of the suture from the suture arms. The second actuator is released for withdrawing the needles and pulling the suture ends through the vessel wall. The first actuator is released for retracting the suture arms. The suturing device is withdrawn from the body and the ends of the suture are tied for closing the incision. In one variation, the first actuator is releasably securable in the depressed position. In another variation, a first follower member is coupled to the suture arms by an actuating rod, wherein depression of the first actuator causes the first follower member to translate longitudinally within the handle portion for causing the arms to deploy. In another variation, a second follower member is coupled to the needles, wherein depression of the first actuator causes the second follower member to translate longitudinally within the handle portion for causing the needles to extend.

BRIEF DESCRIPTION OF THE DRAWINGS

FIG. 3 is a perspective view of the suturing apparatus formed with an improved handle portion.

FIG. 6A is a side view illustrating the relationship between the needle trigger and the second follower member in the handle portion.

DETAILED DESCRIPTION OF THE PREFERRED EMBODIMENTS

The preferred embodiments of the present invention described below relate particularly to closing incisions within biological tissue. While the description sets forth various embodiments and specific details, it will be appreciated that the description is illustrative only and should not to be construed in any way as limiting the invention. Furthermore, various applications of the invention, and modifications thereof, which may occur to those skilled in the art, are also encompassed by the general concepts described below.

Figure 1:
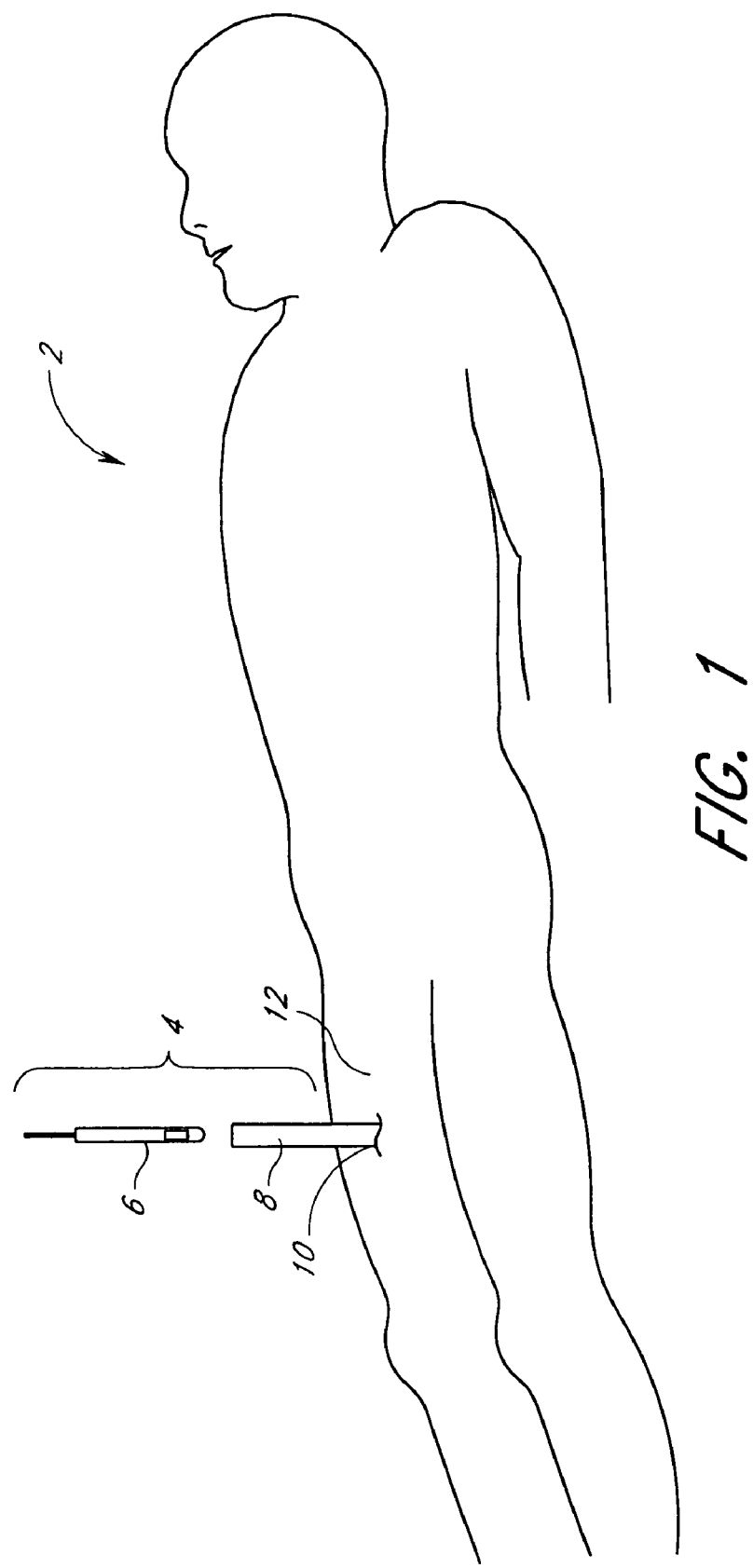
FIG. 1 illustrates one embodiment of a suturing apparatus and related assembly in an exemplifying use environment.
Figure 2:
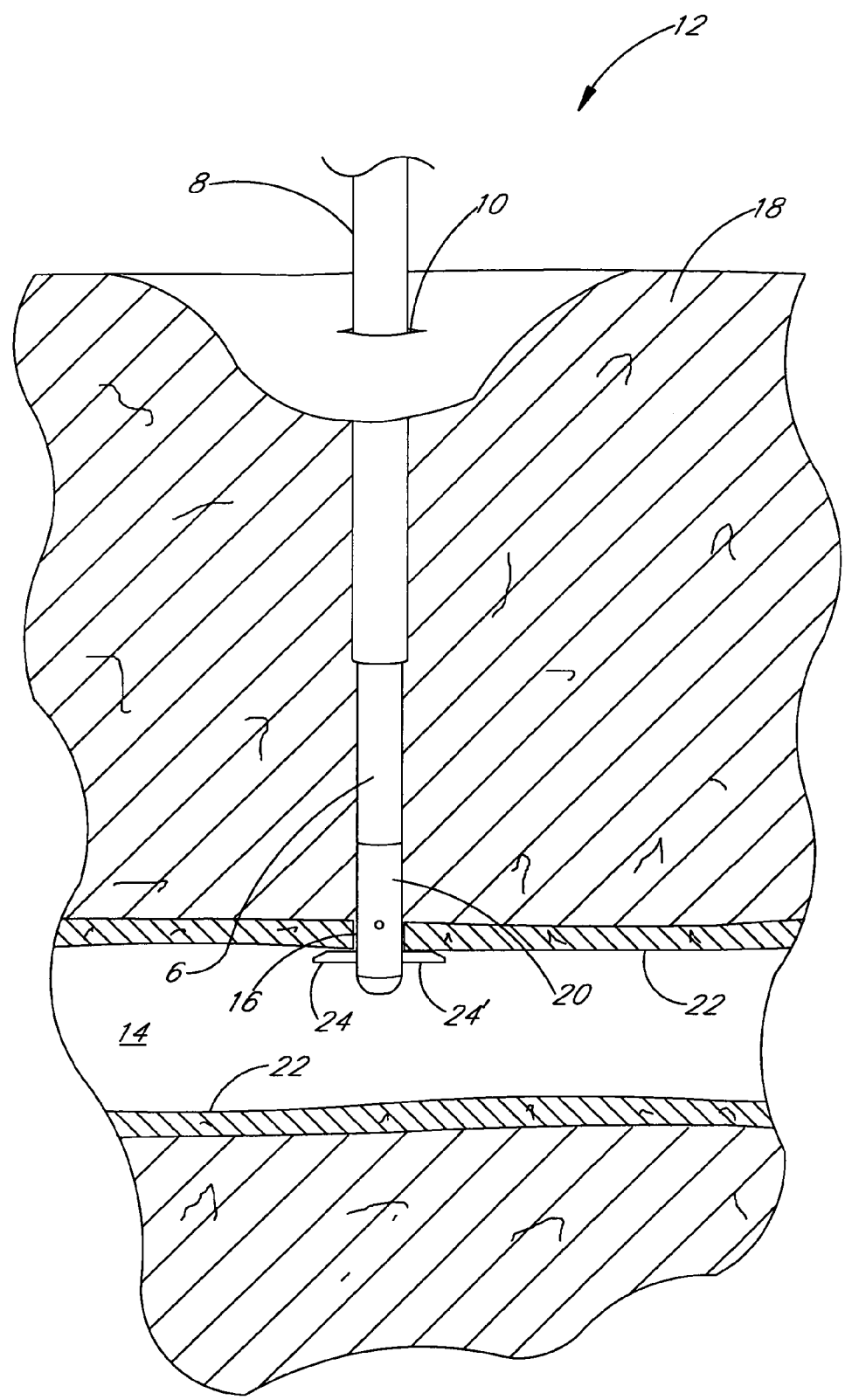
FIG. 2 illustrates an enlarged cross-sectional view of the suturing apparatus in an exemplifying use environment, such as a patient's thigh.

With reference now to FIG. 1, one preferred assembly 4 for closing an incision is illustrated in an exemplifying use environment. The assembly 4 generally comprises a suturing apparatus 6 and a catheter sheath introducer (CSI) 8. The suturing apparatus 6 may be used to seal a blood vessel following an interventional catheterization procedure, such as an angiogram, angioplasty or other procedure. With reference now to FIG. 2, an enlarged view of the treatment site is illustrated. In this view it can be seen that a physician makes an initial incision 10 in an upper thigh region 12 of a patient 2. The physician then inserts a needle (not shown) into the incision 10 such that the needle pierces a femoral artery 14, creating a vessel incision 16 therein. When blood bleeds back from the insertion, the physician knows the needle has entered the femoral artery 14. The physician then inserts a guidewire (not shown) through the needle and into the artery 14. The physician may take the needle out and insert a plastic needle (not shown) over the guidewire once the guidewire is in place. The guidewire may then be taken out.

With the plastic needle in place, the physician can insert the CSI 8. The CSI 8 is typically a single-lumen catheter with a valve located on its proximal end. The valve is configured to prevent extraneous bleed back and/or to introduce medication into the patient's body. The vessel incision 16 provides access for medical instruments and probes inside the arterial vessel 14. An instrument, such as a therapy catheter, may be advanced through the artery 14 via the CSI 8 to perform a procedure within the body.

After the medical procedure has been completed and the instrument (e.g., therapy catheter) has been removed, the physician inserts the suturing apparatus 6 through the CSI 8 such that a suture introducer head 20, distally attached to a hollow elongate body 32, enters the first incision 10, passes through the tissue 18 of the patient's thigh 12, and enters the femoral artery 14 through the vessel incision 16. At this point, the suture arms 24, 24' are deployed and the introducer head 20 of the suturing apparatus is pulled back such that the suture arms contact the inner wall 22 of the femoral artery 14. As described in more detail below, needles are deployed from the introducer head which penetrate the wall 14 of the femoral artery 14 adjacent the incision 16. The needles capture suture ends from the suture arms and the needles are then retracted to withdraw the suture ends back through the wall of the femoral artery. The arms are then retracted and the entire suturing apparatus is withdrawn such that the suture ends may be tied together to close the incision.

With reference now to FIG. 3, a preferred embodiment of the suturing apparatus 6 will be described in more detail. Additional details and methods of operation are described in Applicant's U.S. Pat. Nos. 6,245,079 and 6,562,052, each of which are hereby incorporated by reference in their entirety and are considered to be part of this specification. In addition, each of these patents is attached as an appendix. It will be appreciated that although the device 6 is preferably used for suturing vessel walls 22, the device 6 can be used to suture other tissues such as, by way of example, a patent ductus arteriosus, a patent foramen ovale (PFO), a heart defect, a puncture wound, and the like.

In the embodiment illustrated in FIG. 3, the suturing apparatus 6 generally comprises an elongate body 32, an introducer head 20 and a handle portion 100. The handle portion 100 allows the physician to operate the suturing apparatus such that suture may be applied to an incision in a very quick and easy manner. The handle portion requires very little manipulation during use and may be operated with a single hand if necessary. The suturing apparatus may be used to close an incision located deep within the patient's tissue (e.g., in the femoral artery) without requiring the application of pressure over an extended period of time. As a result, the suturing apparatus may substantially reduce the recovery period following a medical procedure, thereby allowing the patient to return home more quickly and substantially reducing costs. The dimensions of the suturing apparatus 6 may vary according to the suture site and the biological tissue intended to be sutured. In one configuration, the suture introducer head 20 has a diameter of about 0.105 inches, and the hollow elongate body 32 has a diameter of about 0.098 inches.

The handle portion 100 comprises a main housing 102, an arm trigger 104, a needle trigger 106 and an arm release button 108. The arm and needle triggers provide actuators for producing movement of internal components within the main housing, which in turn move at least one arm and needle for applying suture to a treatment site. As will be described in more detail below, the handle portion is constructed such that the arm trigger 104, needle trigger 106 and arm release button 108 may be depressed by the physician in a particular order to extend and retract cooperating suture arms and needles along the introducer head 20 for applying suture to an incision.

The arm and needle triggers are preferably pivotally coupled to the main housing 102 about pin 110 such that the triggers rotate as they are depressed by the physician. As will be described in more detail below, the pivotal rotation facilitates the cam-like interaction of the triggers with the internal components of the main housing. An opening 112 is provided along the main housing 102 for allowing manual retraction of the needles in the event that the needles become stuck in the tissue during retraction. This provides a safety mechanism to ensure that the needles of the suturing apparatus cannot become stuck in the extended position. In one embodiment, a tool (not shown) is inserted through the opening 112 in the main housing 102 for applying force to assist in the retraction of the needles.

Figure 3A:
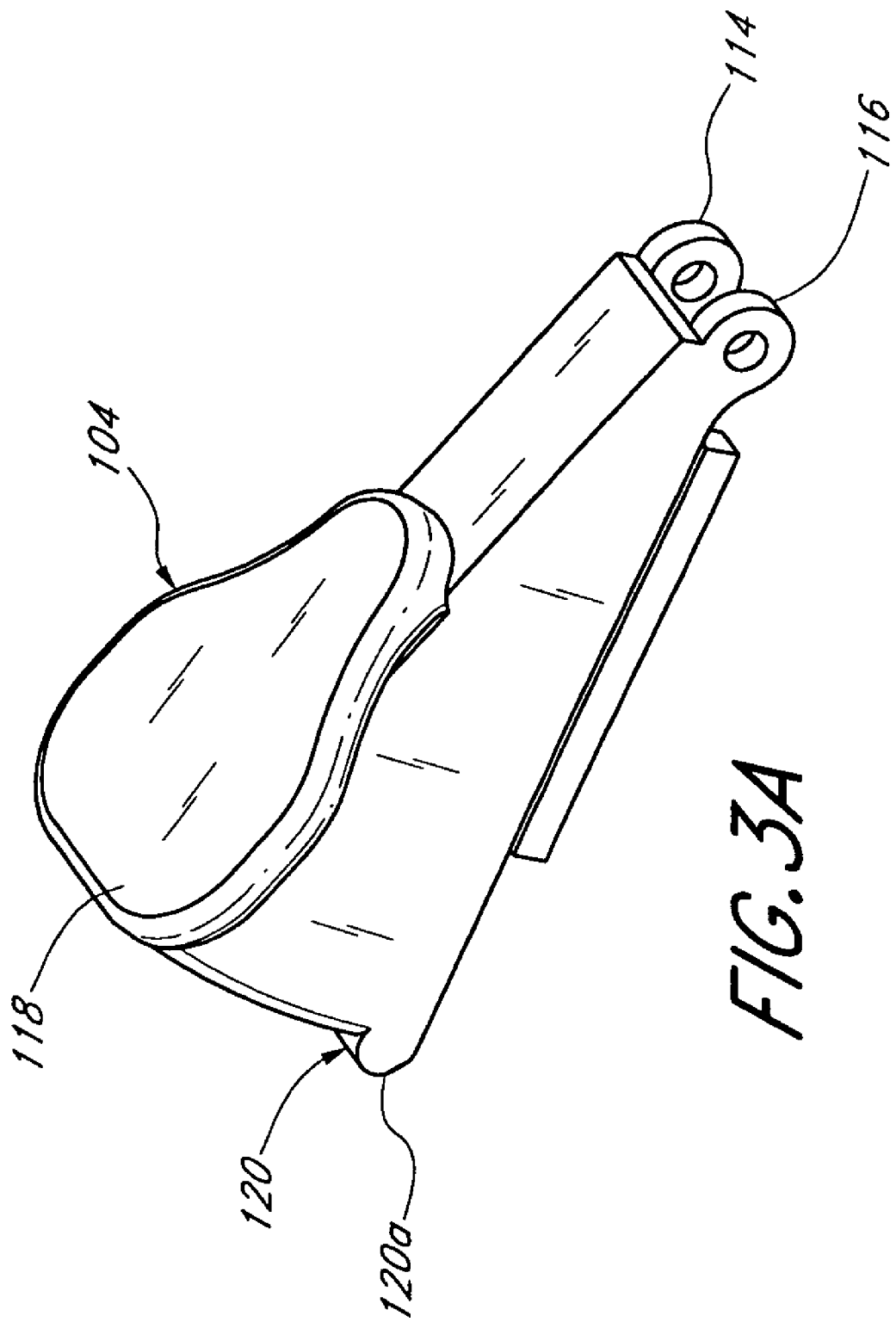
FIG. 3A is a perspective view of an arm trigger, which forms a portion of the handle portion of the suturing apparatus of FIG. 3.

With reference to FIG. 3A, the arm trigger 104 is shown in isolation. Loops 114, 116 are provided along the distal end of the arm trigger for receiving the pin 110 in the main housing. The bottom corner portion 120 along the proximal end portion of the arm trigger is shaped with a protrusion 120A which provides a camming surface for engaging a first slidable follower member in the main housing. The protrusion also allows the arm trigger to be held in the depressed position for locking the arms in the deployed condition. The top surface 118 of the arm trigger is shaped for engagement with the physician's thumb or finger.

Figure 3B:
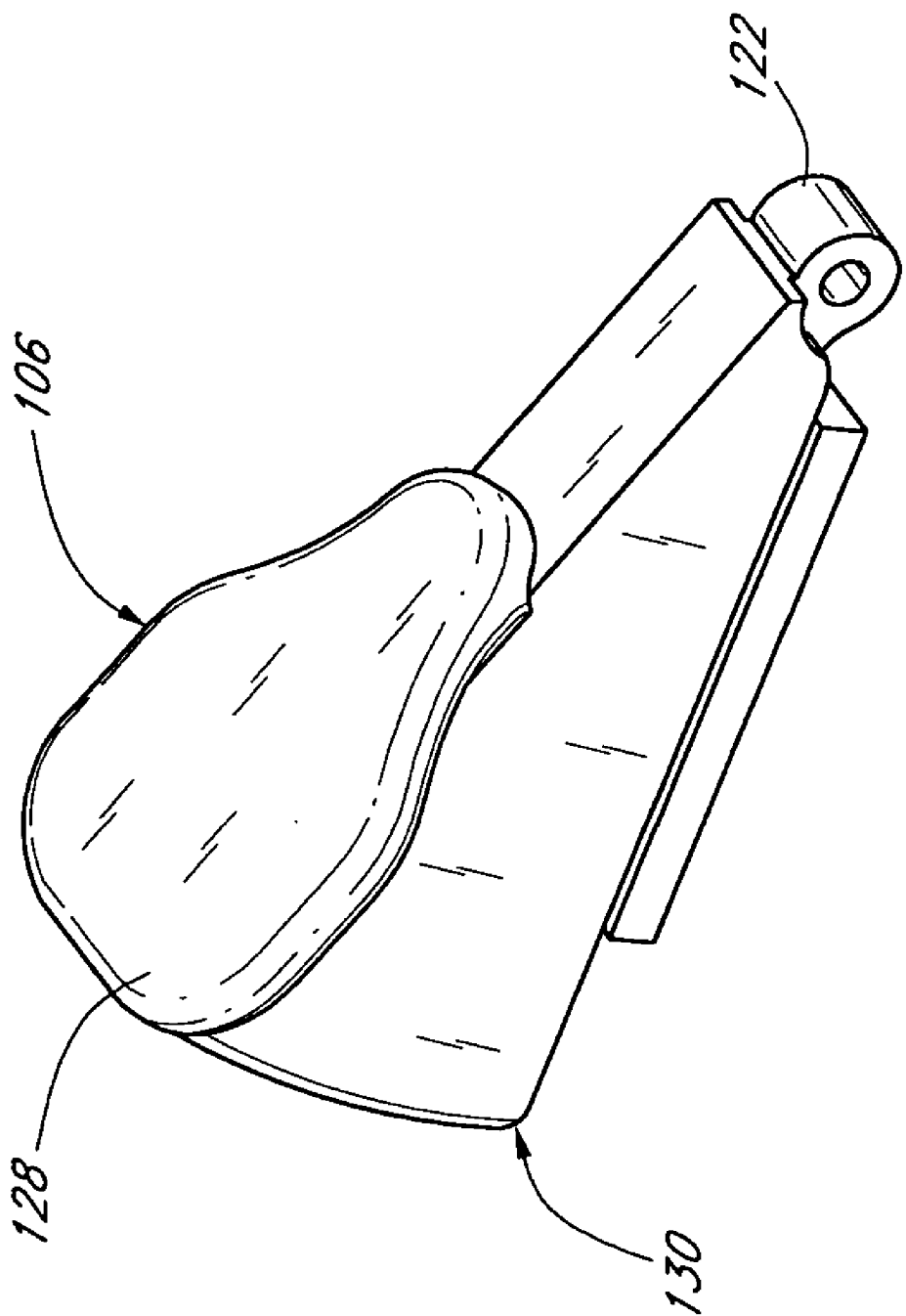
FIG. 3B is a perspective view of a needle trigger, which forms a portion of the handle portion of the suturing apparatus of FIG. 3.

With reference to FIG. 3B, the needle trigger 106 is shown in isolation. Loop 122 is provided along the proximal end of the needle trigger for receiving the pin 110 in the main housing. The loop is shaped to fit within the gap between the loops 114, 116 of the arm trigger 104 (see FIG. 3A). The bottom corner portion 130 along the distal end portion of the needle trigger provides a camming surface for engagement with a second slidable follower member in the main housing. The top surface 128 of the needle trigger is shaped for engagement with the physician's thumb or finger.

Preferred internal components of the handle portion 100 will now be described in more detail. The internal components cooperate with the arm and needle triggers 104, 106 (i.e., actuators) and arm release button 108 for effecting movement of the arms and needles during the application of suture. More specifically, the arm and needle triggers actuate the arms and needles by effecting movement of the internal components contained with the main housing. As described above, the arm and needle triggers each preferably have corner portions 120, 130 shaped with camming surfaces which interact with first and second slidable follower members in the main housing. The follower members are caused to translate longitudinally when the arm or needle triggers are depressed by the physician.

Figure 4:
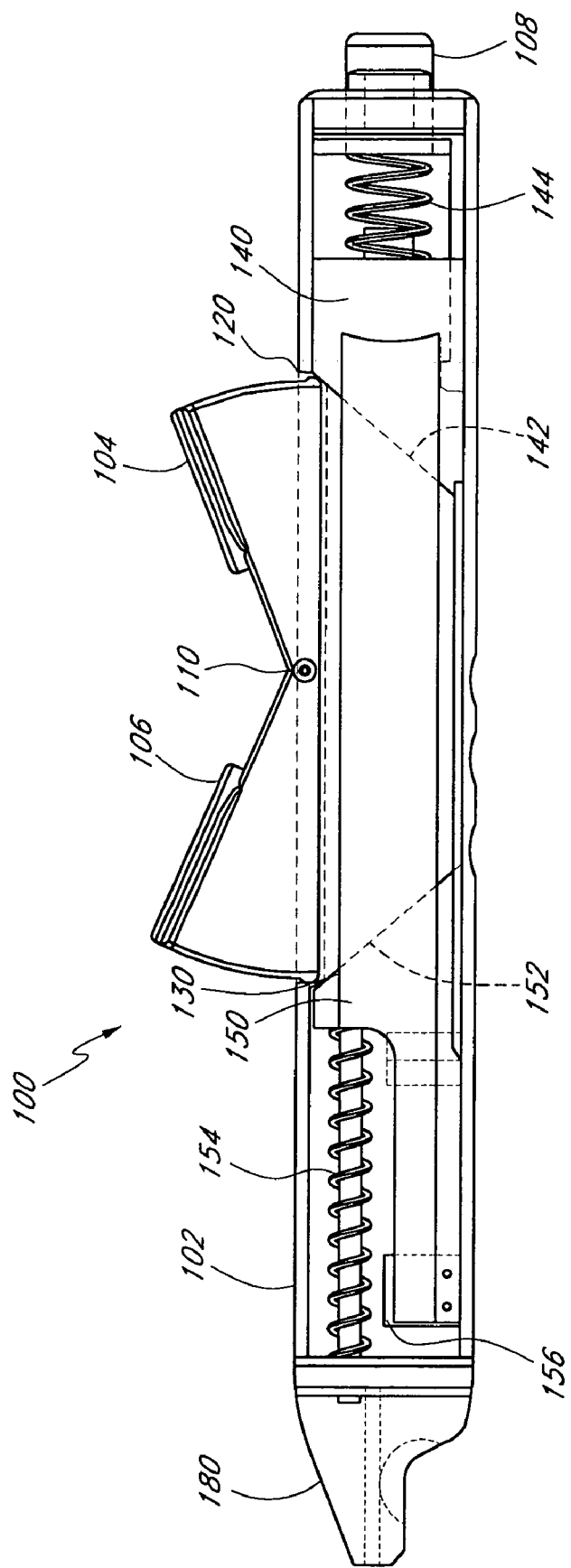
FIG. 4 is a side partial cross-sectional view of the handle portion wherein the arm trigger and needle trigger are in the non-depressed positions.

With reference now to FIG. 4, a cross-sectional side view of the handle portion 100 is shown for purposes of illustration. It can be seen that a first follower member 140 is slidably disposed within the interior of the main housing 102. The first follower member 140 is connected to a proximal end of an actuating rod, preferably through a drive wire tab 156 described below, which extends distally through the main housing and elongate body for connection to each of the arms. When the first follower member 140 is in the distal position, as shown in FIG. 4, the arms are fully contained within the introducer head. However, when the first follower member 140 is moved proximally by the arm trigger 104 (indicated by the arrow in FIG. 5), each of the arms deploys outward through apertures on the sides of the introducer head. (The operation of the arms and needles will be described in more detail below.) Accordingly, longitudinal movement of the first follower member 140 relative to the main housing controls the position of the arms. An arm spring 144 provides a biasing force to maintain the first follower member 140 in the distal position in the absence of any external input. Although one type of arm spring is shown for purposes of illustration, any known biasing mechanisms may be used for maintaining the first follower member 140 into the distal position.

It can be seen that the first follower member 140 is formed with an inclined "cammed" surface 142 along a distal face. As shown in FIG. 4, the inclined cammed surface is configured for engagement with the camming surface along the corner portion 120 of the arm trigger 104. When the arm trigger 104 is depressed, the corner portion 120 of the arm trigger 104 pushes along the inclined surface 142 of the first follower member 140. The downward force acting on the inclined surface results in longitudinal translation of the first follower member. The longitudinal force causes the first follower member to slide in a proximal direction (i.e., backward) within the main housing. As the first follower member slides backward, the actuating rod is pulled in a proximal direction, thereby causing the arms to deploy outward through the ports.

Figure 10:
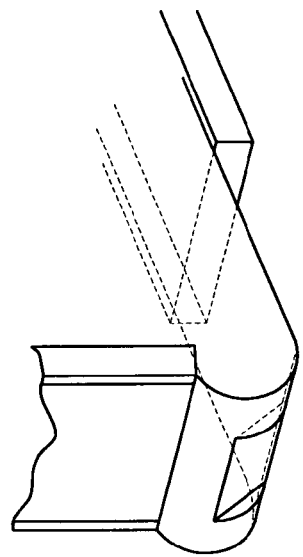
FIG. 10 is another perspective view illustrating a preferred corner portion of the arm trigger wherein the corner portion is provided with a camming surface.
Figure 7:
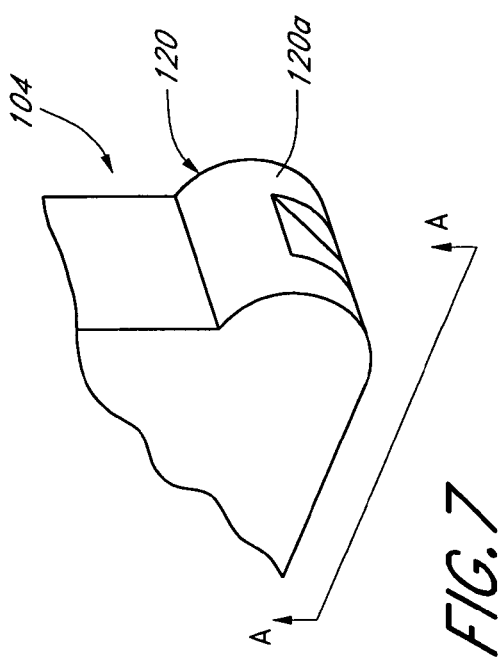
FIG. 7 is a perspective view illustrating a preferred corner portion of the arm trigger wherein the corner portion is provided with a camming surface.

The arm trigger 104 is preferably releasably securable in the fully depressed condition for locking the arms in the deployed condition. As a result, it is not necessary for the physician to apply a constant a force on the arm trigger 104 to maintain the suture arms in the deployed condition. As described above, the corner portion 120 of the arm trigger is preferably formed with a protrusion 120A. FIG. 7 provides an enlarged view of the corner portion 120 including the protrusion 120A. The protrusion is shaped to be captured and held beneath the first follower member 140 when the arm trigger 104 is fully depressed. As discussed above, the arm spring 144 urges the first follower member forward (in the distal direction) such that the first follower member abuts the arm trigger and securely holds the protrusion. Accordingly, the cooperation of the protrusion and the first follower member creates a detent mechanism such that the arm trigger is selectively maintained in the depressed position. FIG. 10 provides another perspective view of the corner portion of the arm trigger.

Figure 8:
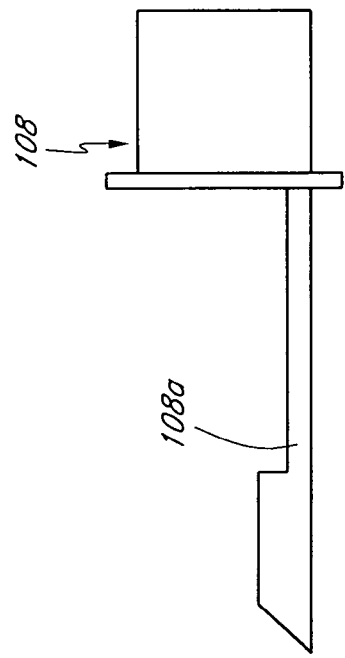
FIG. 8 is a side view illustrating a preferred embodiment of a release button for releasing the arm trigger and thereby retracting the suture arms.
Figure 9:
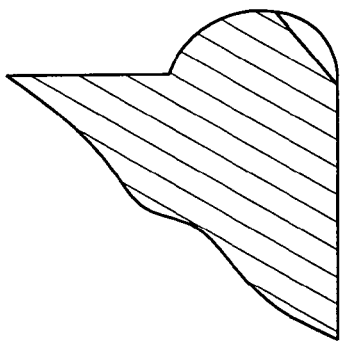
FIG. 9 is a side view illustrating an alternative embodiment of a corner portion of the arm trigger wherein a section is cut away to facilitate the release of the arm trigger.

With reference again to FIG. 4, the arm release button 108 is configured for releasing the protrusion when it is desired to retract the deployable arms. As illustrated, the arm release button 108 is preferably provided along a proximal end of the main housing 102 and is configured for engagement with the arm trigger 104. An arm release spring 144 may be provided for maintaining the arm release button 108 in the non-depressed condition in the absence of an external input. Accordingly, the arm release button can only act on the arm trigger when a sufficient force is applied to overcome the biasing force of the arm biasing spring 144. With reference now to FIG. 8, the arm release button 108 is shown in isolation. The arm release button is provided with an elongate member 108A that is configured to contact the corner portion of the arm trigger when the arm trigger is being held in the fully depressed condition. More particularly, the elongate member 108A is configured to urge the arm trigger in the distal direction such that the protrusion is released from the first follower member. FIG. 9 is a cross-sectional view illustrating an alternative arm trigger wherein a section of the corner portion has been cut away to facilitate the release of the arm trigger upon actuation of the arm release button. It will be appreciated that alternative methods may be used to release the arm trigger. For example, the arm trigger may be provided with a lip on its upper surface and an actuator may be used to engage the lip to pull the arm trigger back to its initial position.

Figure 5:
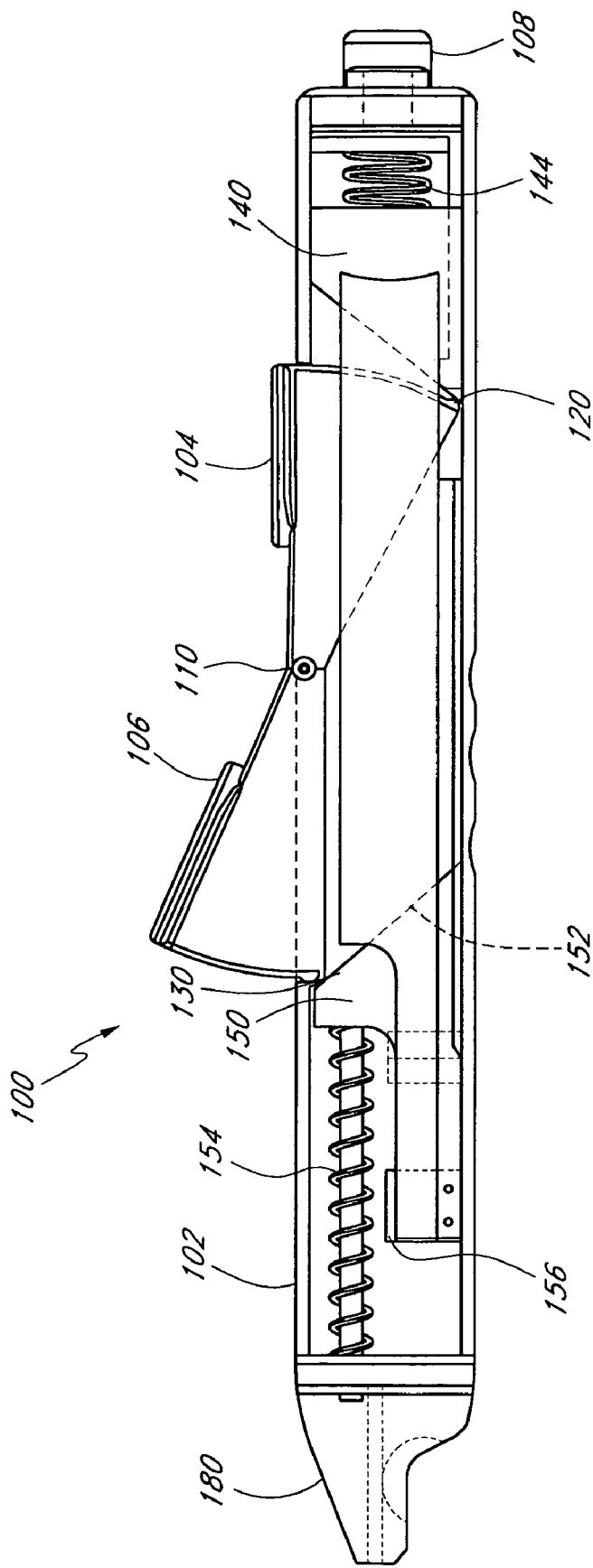
FIG. 5 is a side partial cross-sectional view of the handle portion wherein the arm trigger is fully depressed for locking the suture arms in the deployed condition.

A second follower member 150 is slidably disposed within the interior of the main housing at a location distal to the first follower member 140. The second follower member 150 is connected to the proximal ends of the elongate needles 70, 70'. Thus, longitudinal movement of the second follower member 150 relative to the main housing 102 effects the position of the needles. The second follower member 150 has a proximal position (as shown in FIGS. 4 and 5) wherein the needles are in the retracted (non-deployed condition). A needle biasing spring 154 engages the second follower member for maintaining the second follower member in the proximal position in the absence of any external input. Although one particular embodiment of a needle biasing spring 154 is shown for purposes of illustration, a wide variety of different biasing mechanisms may be used for biasing the second follower member into the proximal position.

The second follower member 150 is provided with an inclined "cammed" surface 152 along the proximal face such that the second follower member cooperates with a camming surface along the corner portion 130 of the needle trigger 106 in a manner substantially similar to that of the first follower member. More particularly, as shown in FIG. 5, the inclined surface is shaped for slidable engagement with a camming surface of the needle trigger 106.

Figure 6:
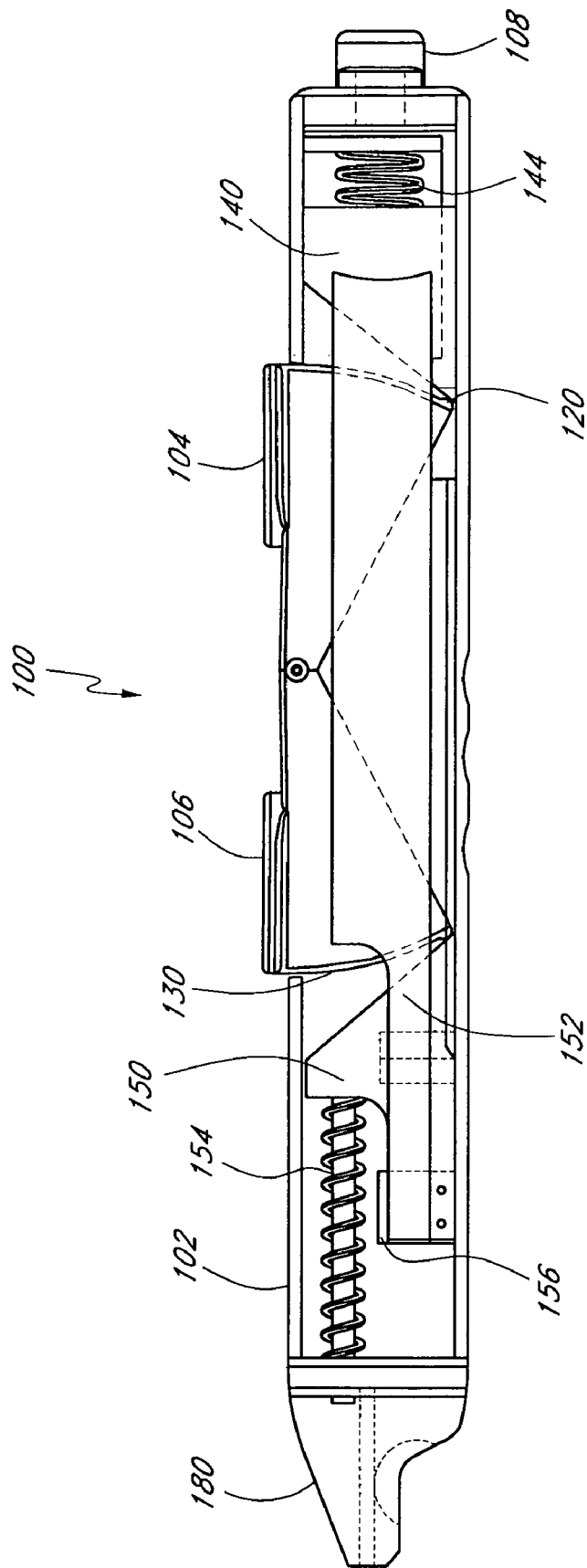
FIG. 6 is a side partial cross-sectional view of the handle portion wherein both the arm trigger and the needle trigger are fully depressed for extending the needles to engage the suture ends held by the suture arms.
Figure 6B:
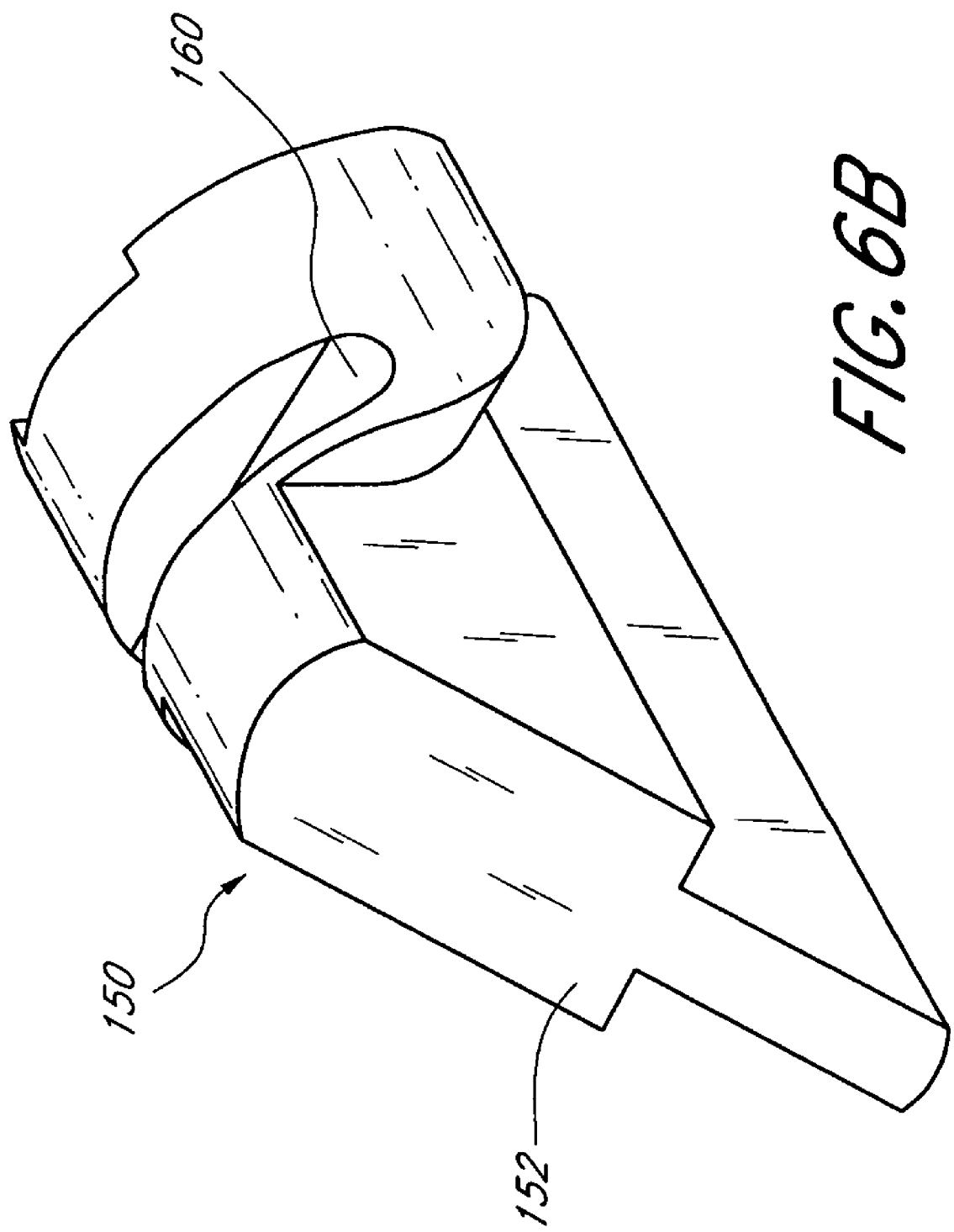
FIG. 6B is a perspective view of the second follower member.

As the needle trigger 106 is depressed, the camming surface along the corner portion 130 of the needle trigger pushes against the inclined surface 152 of the second follower member 150, as illustrated in the cross-sectional view of FIG. 6A. The force from the needle trigger creates a resulting longitudinal force on the second follower member that causes the second follower member to slide distally relative to the main housing. As the second follower member translates distally within the housing (as denoted by the arrow in FIG. 6A), the needles 70, 70' are pushed in a distal direction, thereby causing the distal end portions of the needles to extend outward from the introducer head for engagement with the suture arms. The extension of the needles from the introducer head will be described in more detail below. In preferred embodiments, the second follower member 150 is contained within a body portion that is integral with the first follower member. The body portion provides a slotted track such that the second follower member may be guided proximally and distally during use. Thus, the first and second follower members are preferably slidably coupled to each other. It should also be noted that the second follower member may be formed with a longitudinal lumen for slidably receiving the actuating rod 58. Accordingly, the actuating rod 58 may be slid longitudinally by movement of the first follower member without interfering with the second follower member. FIG. 6B provides a perspective view of the second follower member 150 having an inclined surface 152. It can be seen that the lower portion of the second follower member is thinner in construction. The thinner section is configured to fit within a groove in the body portion for guiding the movement of the second follower member, as described above. The second follower member is also formed with a slot 160 for receiving a tool through the window 112 in the main housing 102 (FIG. 3). The tool may be inserted through the window and into the slot. The tool may then be used to slide the second follower member in the event that it sticks, thereby providing a safety mechanism as described above.

The cammed surface of the first and second follower members is shaped to produce a desired motion in response to actuation of the arm and needle triggers, respectively. In one preferred embodiment, at least a portion the cammed surface of the second follower member is inclined at about 35° or more relative to the longitudinal axis. The angle of inclination is denoted by the symbol $\alpha$ (alpha) in FIG. 6A. In another embodiment, at least a portion of the cammed surface is inclined at about 40° or more relative to the axis. In another variation, at least a portion of the cammed surface is inclined at about 41° relative to the axis. In another variation, at least a portion of the cammed surface is inclined at between about 35-45° relative to the axis. In another variation, at least a portion of the cammed surface is inclined at between about 39-43° relative to the axis. In another variation, at least a portion of the cammed surface is inclined at between about 40-42° relative to the axis. In still another variation, the camming surface is curved. The same preferred ranges also apply to the cammed surface of the first follower member. It will be appreciated that the ratio of trigger movement to needle movement is proportional to the angle of the inclined surface. It has been found that the above angles provide excellent performance while minimizing the diameter of the handle portion. For example, a lower angle would make the follower members more difficult to move due to frictional forces. On the other hand, a higher angle would necessitate a larger follower member in order to produce the same amount of longitudinal translation, thereby necessitating a larger (e.g., larger diameter) handle portion. Furthermore, it has been found that an inclined surface formed with a substantially constant angle provides a substantially directly proportional relationship between trigger movement and needle movement. As a result, the physician is able to advance and retract the needles with great precision and predictability by controlling the movement of the needle trigger.

With reference again to FIGS. 4 through 6, the main housing 102 is preferably constructed of a translucent or transparent material, such as plastic, such that the movement of the components within the main housing is visible to the physician. The transparency advantageously provides visual feedback to the physician regarding operation of the suturing apparatus. If desired, markings or other indicia may be provided such that the position of the needles may be easily perceived during use. Alternatively, a window may be provided for observing the movement of the internal components or a portion of one or more internal components may extend through the main housing to an exterior surface for purposes of visibility.

Figure 11A:
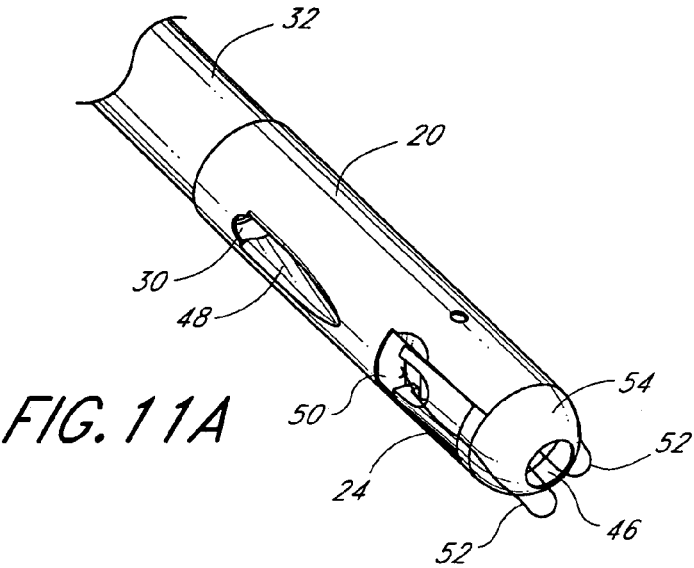
FIG. 11A is an enlarged perspective view of the distal end portion of the suturing apparatus of FIG. 3.
Figure 11B:
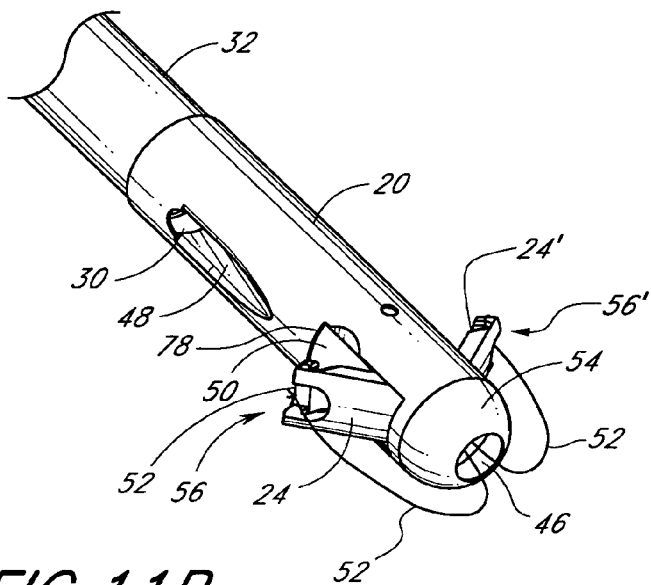
FIG. 11B is perspective view of the distal end portion of FIG. 11A with a pair of suture arms partially deployed.
Figure 11C:
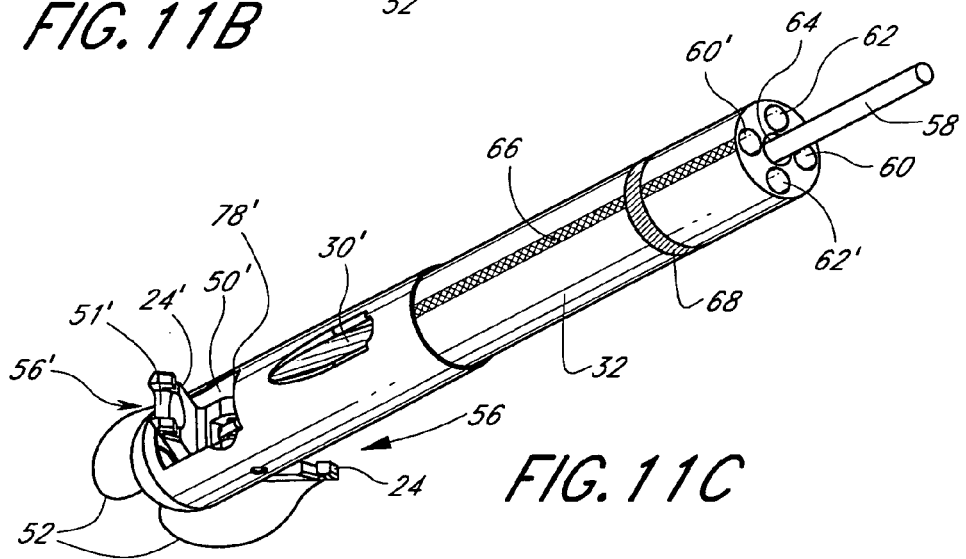
FIG. 11C is a rear perspective view of the distal end portion of FIG. 11A with a pair of suture arms partially deployed.

With reference to FIGS. 11A through 11C, the distal end portion of the suturing apparatus will now be described in more detail. The illustrated distal end portion provides one preferred embodiment that may be operated using the improved handle portion described above. As shown, the distal end portion comprises the suture introducer head 20, a pair of suture arms 24, 24', a pair of suture clasps 56, 56', a pair of suture arm apertures 50, 50', a pair of curved or slanted needle guides 48, 48', a pair of needle apertures 30, 30', a distal end 54, a hole 46, a suture 52 and an actuating rod 58. The distal end portion further comprises a pair of needles 70, 70' (see FIGS. 13 through 15). When the suture arms 24, 24' are retracted into the suture arm apertures 50, 50' and the needles 70, 70' are retracted into the needle apertures 30, 30', the arms 24, 24' and the needles 70, 70' are recessed within the suture introducer head 20, as shown in FIG. 11A. This prevents the arms 24, 24' and the needles 70, 70' from causing tissue damage while the distal end portion passes through a biological structure.

Figure 15:
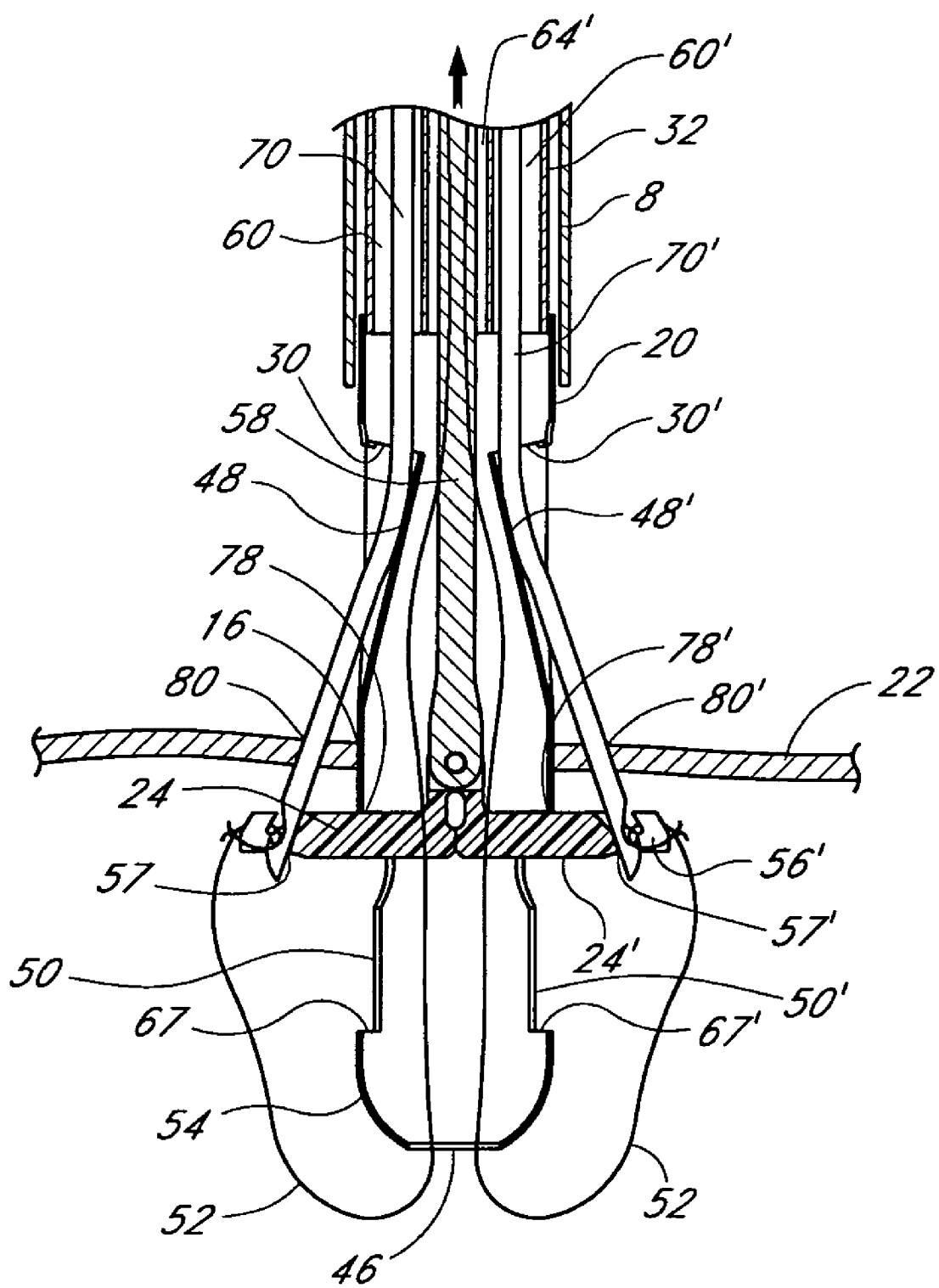
FIG. 15 is a cross-sectional view of the suturing apparatus of FIG. 3 with a pair of suture arms fully deployed and a pair of needles engaging the suture arms.

FIGS. 11B and 11C illustrate the distal end portion of the device 6 (FIG. 3) with the suture arms 24, 24' partially deployed outwardly from their recessed positions. Such deployment is achieved by partially depressing the arm trigger 104, as described above with reference to FIGS. 4 through 6. Depressing the arm trigger 104 translates the first follower member 140 (FIG. 4) and actuating rod 58 proximally, which brings the suture arms 24, 24' into contact with a pair of proximal inside edges 78, 78' of the suture arm apertures 50, 50'. As the arm trigger is depressed further, the proximal inside edges 78, 78' force the suture arms 24, 24' into a deployed state. In one embodiment, the suture arms 24, 24' continue to deploy radially until the arms 24, 24' are substantially parallel with each other and substantially perpendicular to the longitudinal axis of the suture introducer head 20, as shown in FIG. 15. In other embodiments, the suture arms 24, 24' may be "fully" deployed when they reach an acute or obtuse angle relative to each other.

As shown most clearly in FIG. 11B, each of the suture arms 24, 24' comprises a suture clasp 56, 56' which holds an end of the suture 52. Each of the suture arms 24, 24' are pre-loaded with the ends of the suture 52 before operation. The ends of the suture 52 then pass from the suture clasps 56, 56' to the hole 46 whereby the ends of the suture 52 enter the suture introducer head 20 and are passed proximally through the hollow elongate body 32. In the embodiment illustrated in FIG. 11B, each end of the suture 52 has a capture portion comprising a loop which is tied onto the ends of the suture claps 56, 56'. It is contemplated, however, that the capture portions are not restricted solely to tied loops, rather other types of capture portions may be utilized such as, by way of example, spheres or ferrules.

Figure 12A:
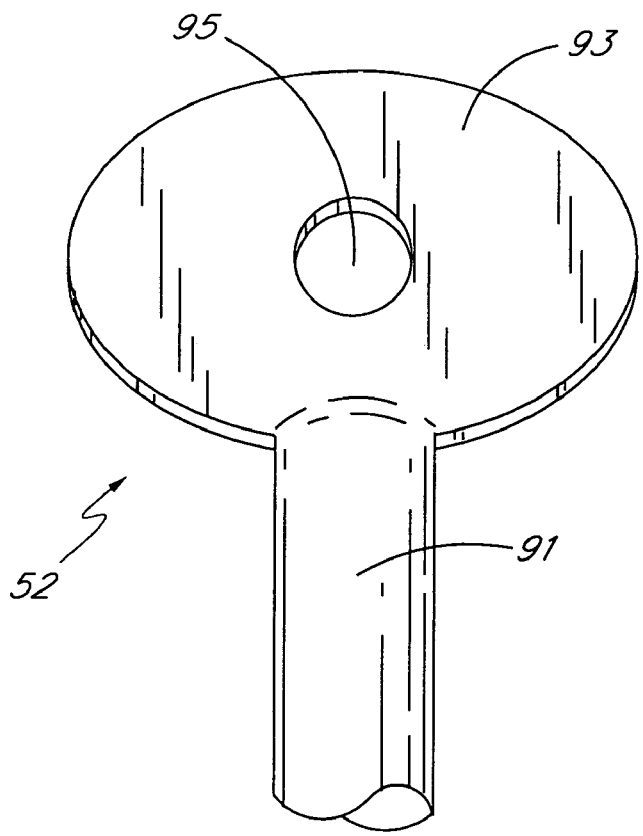
FIG. 12A is a perspective view of a suture end having a flattened distal portion with an eyelet.

FIG. 12A illustrates another embodiment of a capture portion wherein the end of the suture 52 comprises a flattened distal region 93 having a hole or eyelet 95. In the embodiment illustrated in FIG. 12A, the suture 52 comprises a strand 91 of deformable material that is preferably monofilament, such as Deklene (from Genzyme), Prolene (from Johnson & Johnson), or Nylon (from Johnson & Johnson). In one embodiment, the strand 91 is advantageously approximately 0.010" thick and has a length that makes it suitable for use in suture procedures.

In the formation of the flattened distal portion 93, the distal end of the strand 91 is heated until the distal end melts or is otherwise plastically or thermally deformed to form a locally deformed region (such as a globule) that is broader than the rest of the strand 91 in at least one dimension (i.e., at least one dimension of the strand 91 has been increased). Once the deformed region is formed, the strand 91 may be allowed to cool, and the deformed region may then be flattened by use of a die. The die preferably has a relief or recessed portion for accepting the strand 91 and the deformed region. A block, which preferably also has a recessed portion that mates with the recessed portion, may then be placed over the deformed region. The deformed region is then squeezed between the die and the block, resulting in the formation of the flattened distal portion 93 illustrated in FIG. 12A. The flattened distal portion 93 preferably has a thickness that matches the rest of the strand 91. The edges of the flattened distal portion 93 may then be trimmed to form a smooth disc portion to reduce the risk of such edges snagging on vessel walls during suturing procedures.

As illustrated in FIG. 12A, the eyelet 95 is formed within the flattened distal portion 93. A punch (not shown) such as a hypotube may be used to poke through the flattened distal portion 93, thereby leaving the eyelet 95 within the flattened distal portion 93. The eyelet 95 is formed such that a surgical hook or needle may pass through the eyelet 95 in a suturing procedure. The flattened distal portion 93 acts as a connector to the hook or needle, allowing the strand 91 to be picked up by the hook or needle. The method of forming the eyelet 95 described herein, including the forming of the flattened distal portion 93, advantageously results in no significant reduction in the mechanical strength of the strand 91, with the material throughout the strand 91 (including the material in the flattened distal portion 93) having substantially uniform mechanical strength. Methods for forming the flattened distal region 93 are discussed in greater detail in Applicant's above-mentioned U.S. Pat. No. 6,562,052, entitled SUTURING DEVICE AND METHOD.

Figure 12B:
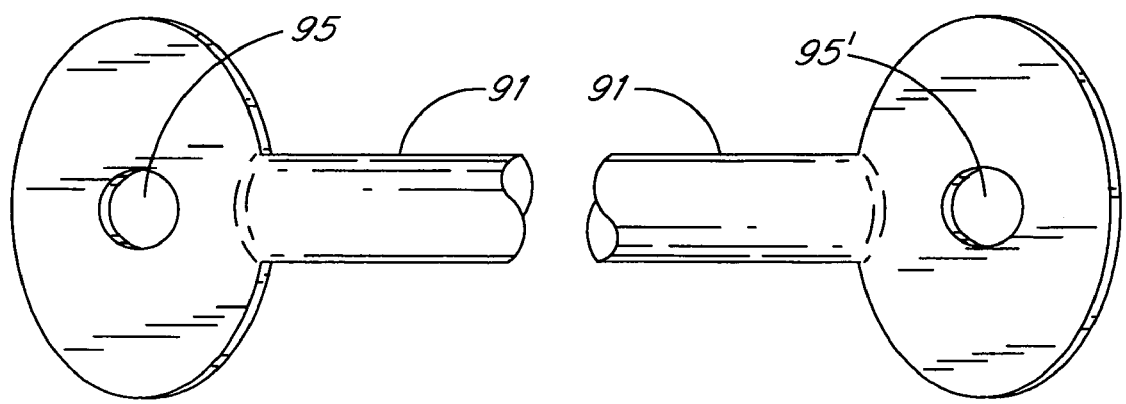
FIG. 12B is a perspective view of distal and proximal ends of a suture each having a flattened distal portion with an eyelet.

Advantageously, the suture embodiment shown in FIG. 12A has no knots or ties formed therein which might increase the profile of the suture strand 91 or make it easier for the suture 52 to snag during use. This process may advantageously be repeated at the proximal end of the strand 91, resulting in eyelets 95, 95' at both ends of the strand 91, as illustrated in FIG. 12B. The flattened distal portion 93 at one or more of the ends of the strand 91 may be bent (not shown) at an angle with respect to the rest of the strand 91 to facilitate the guiding of a surgical needle through the eyelet 95.

FIG. 11C illustrates one preferred configuration of the hollow elongate body 32 which comprises five lumens. Two of the lumens 60, 60' are used to house the needles 70, 70'. Once the suture arms 24, 24' have been deployed, as discussed with reference to FIGS. 11B and 11C (and in greater detail below), the needle trigger 106 (FIG. 3) can be depressed to advance the needles 70, 70' from a recessed position within the suture introducer head 20 to a distally extended position (see FIG. 15). In one embodiment, the needles 70, 70' move distally at substantially the same time. In another embodiment, the needles 70, 70' may be actuated separately such that one of the needles 70, 70' advances before the other.

When the two needles 70, 70' move distally, the needle guides 48, 48' direct the needles 70, 70' out of the needle apertures 30, 30' at an angle relative to the longitudinal axis of the suture introducer head 20, as illustrated in FIG. 15. The needles 70, 70' are flexible and preferably made of a material with shape memory, such as SUPERFLEX NITINOL™. Alternatively, the needles 70, 70' may be comprised of spring steel, surgical stainless steel or any variation thereof. Each of the needles 70, 70' preferably has a diameter of about 0.019 inches, but needles with other diameters may be used in accordance with the particular medical procedure contemplated.

When the needles 70, 70' advance distally, as discussed above, the needle guides 48, 48' cause the needles 70, 70' to bend radially outward. As shown most clearly in FIG. 15, a further outward, radial bend preferably is imparted to the needles 70, 70' when they come into contact with a pair of angled surfaces 57, 57' of the suture arms 24, 24'. When the needles 70, 70' are retracted into the needle lumens 60, 60', the needles 70, 70' resume a straight configuration as a result of their resiliency. Although the embodiment of FIGS. 11A through 15 preferably comprises flexible needles 70, 70', which bend during deployment, it is contemplated that other embodiments may advantageously comprise rigid needles which may be permanently straight or curved.

Referring again to FIG. 11C, the hollow elongate body 32 contains a central lumen 64 which is used to house the actuating rod 58. Another lumen 62 is used to house the length of the suture 52 to prevent the suture 52 from becoming tangled. Alternatively, the suture 52 may be passed through the central lumen 64 along with the actuating rod 58.

A fifth lumen 62' is preferably used for "bleed back," which enables the physician to determine whether the distal end 54 of the suture introducer head 20 is positioned within the artery 14. Bleed back is accomplished through the hole 46 at the distal end 54 of the suture introducer head 20, the suture arm apertures 50, 50' and any other openings in the suture introducer head 20. The direction of blood flow for bleed back is indicated by three dashed arrows in FIG. 13. If the distal end 54 of the suture introducer head 20 is positioned within the artery 14, blood pressure due to blood entering into the hole 46 will be much greater than if the distal end 54 is not within the artery 14. In one embodiment, the lumen 62' extends to a port (not shown) at a proximal portion of the device 6, whereby the physician can determine the blood pressure within the bleed back lumen 62' by monitoring blood flow from the port. For example, the lumen 62' may be attached to a balloon which inflates when the distal end 54 of the suture introducer head 20 passes into the blood vessel 14. In another embodiment, a pressure sensor may be coupled with the lumen 62' to provide the physician with a numeric blood pressure reading. Alternatively, the lumen 62' may be used to inject medication or for diagnostic purposes.

In a preferred embodiment, two thin stripes 66 (only one shown in FIG. 11C) marked on the exterior of the hollow elongate body 32 extend along the entire length of the hollow elongate body 32. The stripes 66 provide a visual indication of the circumferential location of the needles 70, 70' relative to the hollow elongate body 32. The stripes 66 facilitate aligning the needles 70, 70' with the axis of the blood vessel 14, so that needle incisions 80, 80' (see FIG. 15) formed in the vessel wall 22 by the needles 70, 70' will be aligned along a dimension transverse to the flow of blood within the artery 14. This enables the physician to place the suture 52 within the vessel wall 22 such that the suture 52 closes the incision 16 transversely to the blood flow. This is the most efficient direction to close the incision 16. Proper insertion of the needles 70, 70' reduces the risk of damage to the vessel wall 22. Alternatively, the hollow elongate body 32 may have only one stripe 66 which denotes the circumferential location of one of the two needles 70, 70'. Because the needles 70, 70' deploy from opposite sides of the suture introducer head 20, knowledge of the location of one needle provides the physician with knowledge of the location of the other needle.

As illustrated in FIG. 11C, the exterior surface of the hollow elongate body 32 includes a marker 68 which denotes a proximal position to which the CSI 8 should be partially withdrawn (after the distal portion 26 of the suturing apparatus 6 has been inserted into the blood vessel 14) to expose the needle apertures 30, 30'. The partial withdrawal of the CSI 8 is discussed in detail in Applicant's above-mentioned U.S. Pat. No. 6,562,052, entitled SUTURING DEVICE AND METHOD. The marker 68 is shown as a visual marker, but may additionally or alternatively be in the form of a ridge, groove, or other physical structure which interacts with a corresponding structure of the CSI 8 to allow the physician to position the CSI 8 using a sense of feel. For example, the CSI 8 and the hollow elongate body 32 could be configured to releasably engage or interlock with one another when the CSI 8 reaches a predetermined position along the elongate body 32. It is contemplated that a specially formed CSI 8 comprises such an interlocking structure, and is included within the scope of the invention. It is further contemplated that one or more additional markers (not shown) may advantageously be provided along the length of the hollow elongate body 32, distal to the marker 68, to indicate other positions of the CSI 8 relative to the elongate body 32, such as the position at which the suture arms 24, 24' are exposed outside the CSI 8.

The use and operation of the suturing apparatus will now be described with reference to FIG. 3 through 15. From the following description, it will be understood that the handle portion 100 provides an improved mechanism for quickly and easily actuating the components of the suturing apparatus to apply suture to an incision, such as to close a vessel wall after a surgical procedure.

Figure 13:
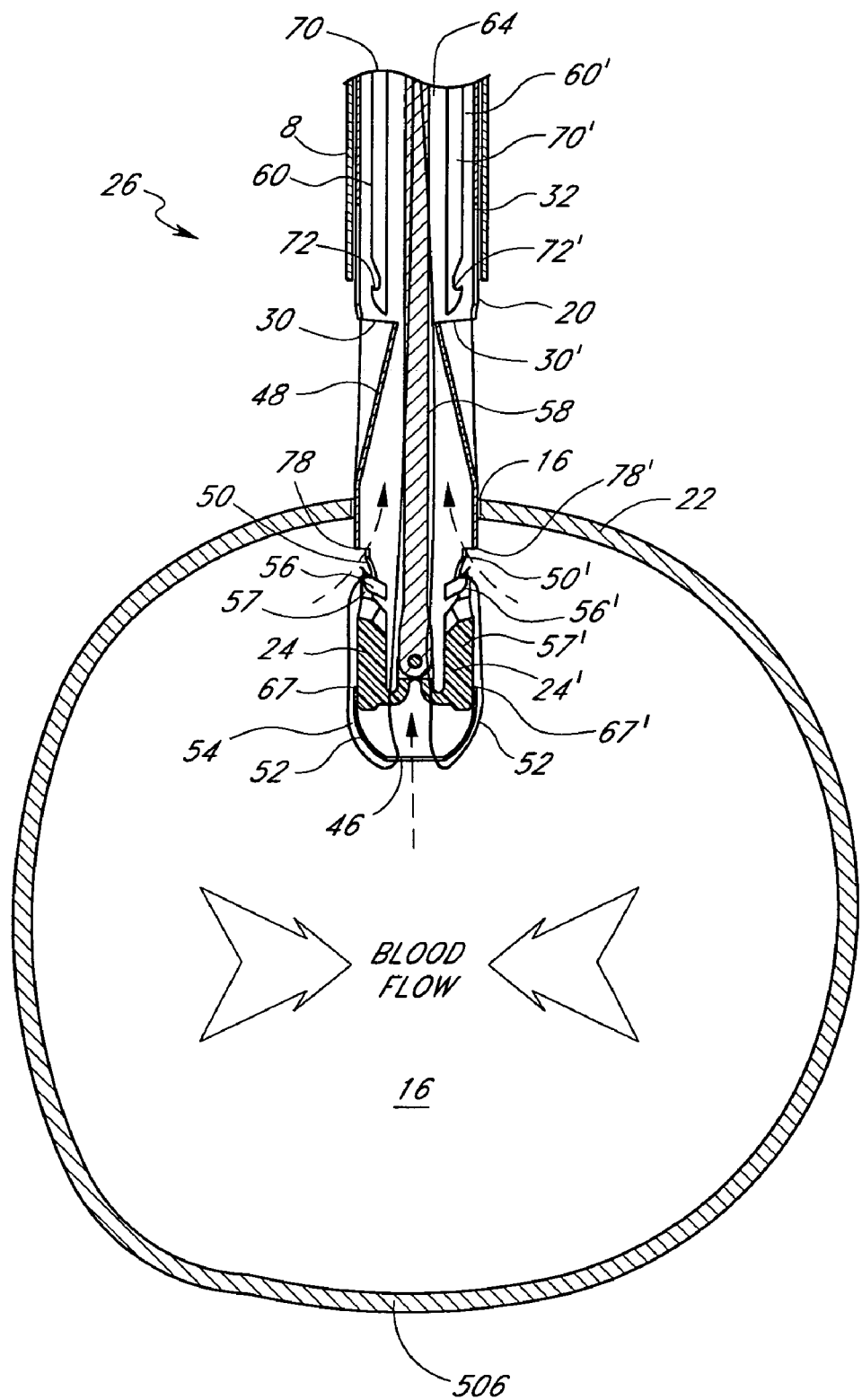
FIG. 13 is a cross-sectional view of the suturing apparatus of FIG. 3 with the distal end portion inserted through an arterial wall.

Before the procedure, the suture arms 24, 24' are pre-loaded with the ends of a suture, such as, for example, a polypropylene suture. Specifically, each end of a suture has a capture portion comprised of a loop, a sphere or a ferrule. In one embodiment, the loop, sphere or ferrule may be formed (e.g., by heat molding) with the same suture material as the length of suture. In another embodiment, the loop, sphere or ferrule may be a separate piece attached (e.g., molded, glued, etc.) onto each end of the length of suture. The loop, sphere or ferrule is loaded in respective suture end supports of the arms 24, 24'. The remaining length of the suture preferably extends through the hollow elongate body. With the CSI 8 extending into the patient's artery 14, the physician then inserts the suture introducer head 20 through the CSI 8 and into the artery 14. The CSI 8 is then partially withdrawn along the hollow elongate body 32 to remove the CSI 8 from the artery 14 and to expose the needle apertures 30, 30', as shown in FIG. 13. The markers 68 (FIG. 11C) on the exterior surface of the hollow elongate body 32 indicate how far the physician should withdraw the CSI 8 to expose the needle apertures 30, 30'.

The distal end 54 of the suture introducer head 20 has a smooth, rounded surface which prevents injury to the opposite vessel wall 22 when the suture introducer head 20 is inserted into the artery 14. In addition, blood flow within the artery 14 is uninterrupted because the suture introducer head 20 does not occlude the artery 14. The physician may use bleed back through the hole 46 and the lumen 62' (FIG. 11C) to determine when the suture introducer head 20 has entered into the artery 14.

During insertion into the artery, the arm trigger 104 and needle trigger 106 are each in the non-depressed positions, as depicted in FIG. 4. As a result, the first follower is located in the distal position such that the suture arms are in the retracted condition. Also, the second follower is in the proximal position such that the needles are in the retracted condition.

While the suture introducer head 20 is inserted into the artery 14, as shown in FIG. 13, the actuating rod 58 holds the suture arms 24, 24' in a recessed state within the suture introducer head 20. The actuating rod 58 applies a downward force while a pair of deflection surfaces 67, 67' of the suture introducer head 20 apply an inward force on each of the suture arms 24, 24', respectively. The combination of these two forces retains the suture arms 24, 24' within the suture arm apertures 50, 50' of the suture introducer head 20. Each of the suture clasps 56, 56' comprises an angled slot which holds a looped end of the suture 52 as illustrated in FIGS. 11A through 11C. The looped ends of the suture 52 are held securely by the suture clasps 56, 56', but are positioned for easy removal by a pair of suture catches 72, 72' at the tips of the needles 70, 70'.

Figure 14:
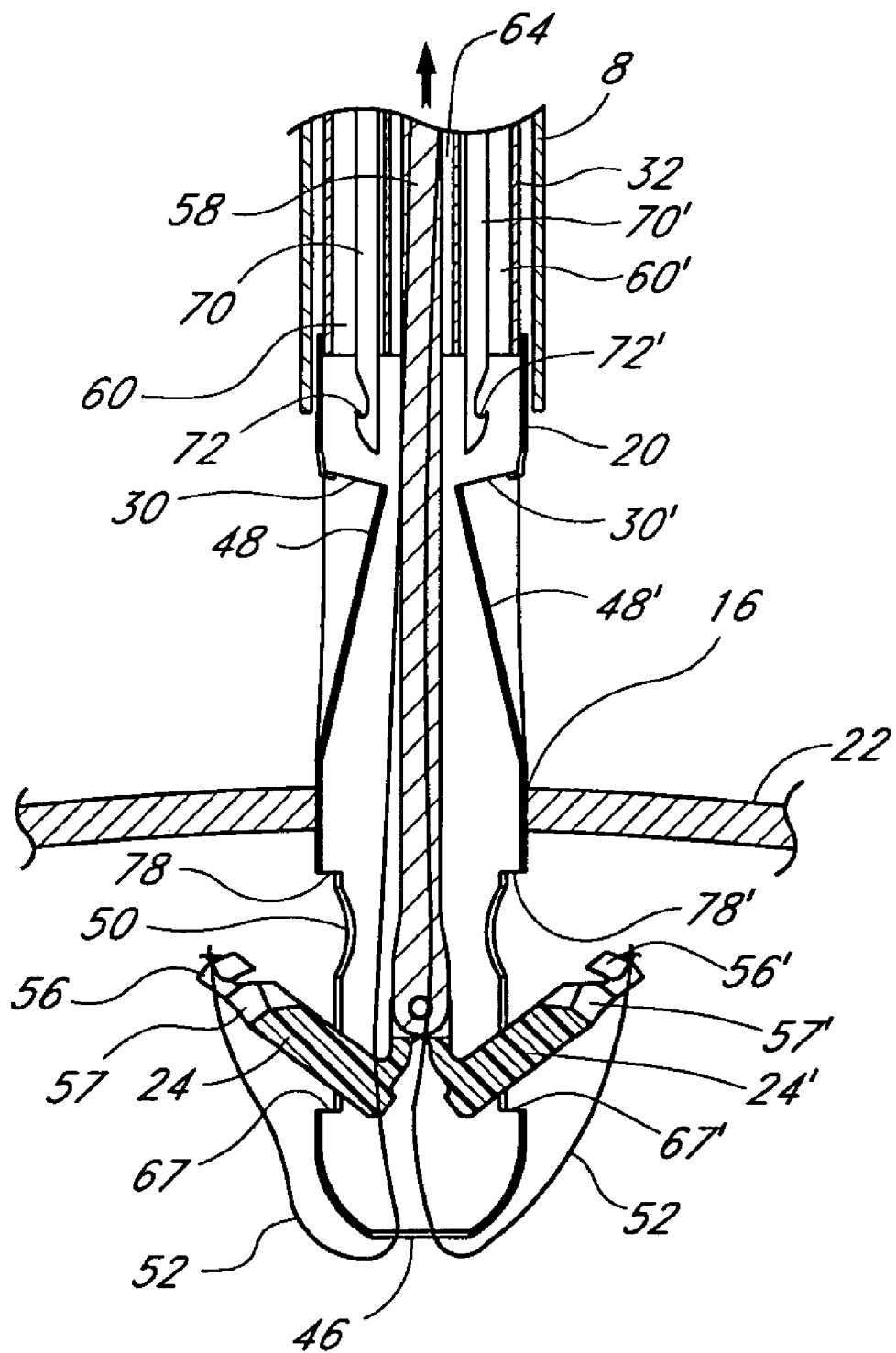
FIG. 14 is a cross-sectional view of the suturing apparatus of FIG. 3 with the distal end portion inserted through an arterial wall and a pair of suture arms partially deployed.

Once the distal portion 26 of the device 6 is properly positioned within the artery 14, the physician depresses the arm trigger 104 (FIG. 3) to deploy the suture arms 24, 24' as shown in FIG. 14. Downward movement of the arm trigger acts on the first follower member 140 in the main housing 102, thereby causing the first follower member to translate proximally, which pulls the actuating rod proximally. The corner portion 120 of the arm trigger 104 provides a camming surface which engages an inclined cammed surface on the first follower member 140. During this action, the force applied on the arm trigger must be sufficient to overcome the biasing force of the arm spring 144. Movement of the first follower member 140 translates the actuating rod 58 proximally, which relieves the downward force applied by the actuating rod 58 and thus also relieves the inward forces applied to the suture arms 24, 24' by the deflection surfaces 67, 67'. This allows the suture arms 24, 24' to assume a partially deployed state as illustrated in FIG. 14. As the physician continues depressing the arm trigger 104, the actuating rod 58 continues translating proximally, bringing the suture arms 24, 24' into contact with the proximal inside edges 78, 78'. The proximal inside edges 78, 78' apply a downward force on each of the suture arms 24, 24', respectively, thereby forcing the suture arms 24, 24' into a fully deployed state as illustrated in FIG. 15.

With reference now to FIG. 5, as the arm trigger 104 becomes fully depressed, the protrusion 120A along the corner portion 120 of the arm trigger 104 advances beneath the first follower body 140. In this position, the arm trigger 104 is maintained in the fully depressed position by the force of the arm spring 144, which pushes the first follower body against the arm trigger. Accordingly, the cooperation between the arm trigger and the first follower body advantageously provides a releasable detent mechanism for holding the arm trigger in the depressed position. When the arm trigger is held in the fully depressed condition, the suture arms 24, 24' are locked in the fully deployed condition.

In the locked state, the suture arms 24, 24' preferably have reached a fully extended position and are longitudinally aligned with each other, as illustrated in FIG. 15. With the suture arms 24, 24' in this fully extended position, the physician may gently slide the suturing apparatus 6 proximally so that the suture arms 24, 24' contact the interior surface of the vessel wall 22.

At this juncture, the physician depresses the needle trigger 106 on the handle portion 100 to distally advance the needles 70, 70' and capture the ends of the suture 52 from the suture clasps 56, 56'. FIG. 5 illustrates the needle trigger in the non-depressed position. FIG. 6 illustrates the needle trigger in the fully depressed position. During downward depression of the needle trigger, the camming surface along the corner portion 130 of the needle trigger 106 engages and slides along the cammed surface of the second follower member 150, thereby causing the second follower member to slide longitudinally within the main housing 102 in a distal direction. During this action, the force applied on the needle trigger 106 must be sufficient to overcome the biasing force of the needle biasing spring 154. As the needle trigger is depressed further, the second follower member continues to slide distally, thereby advancing the needles distally through the main housing and through the hollow elongate body. As the first and second needles advance distally, the distal ends of the needles extend outward for engagement with the arms.

The paths taken by the needles 70, 70' are illustrated in FIG. 15. The needles 70, 70' slide along the needle lumens 60, 60' and out of the suture device 6 through the needle apertures 30, 30', respectively. When the needles 70, 70' come in contact with the needle insertion guides 48, 48', the needles 70, 70' begin to bend radially outward. As the needles 70, 70' exit, they are guided at a radially outward, acute angle away from the actuating rod 58 by the needle insertion guides 48, 48'. The angle of the needle deflection is preferably about 13.2 degrees. Deflection angles between about 10 degrees and about 15 degrees and between about 5 degrees and about 20 degrees are also contemplated.

During advancement, the needles 70, 70' penetrate the vessel wall 22 at an angle, thereby creating the needle incisions 80, 80' on opposite sides of the incision 16. As mentioned above, the needles 70, 70' also preferably bend slightly (radially outward) when they come in contact with the suture arms 24, 24'. The angled surfaces 57, 57' of the suture clasps 56, 56' and the suture catches 72, 72' exert a force on each of the looped ends of the suture 52 such that the looped ends remain tied to the suture clasps 56, 56' while the needles 70, 70' pass therein.

The physician depresses the needle trigger 106 until the suture catches 72, 72' of the needles 70, 70' engage the suture clasps 56, 56' and capture the looped ends of the suture 52. As shown in FIG. 15, the suture arms 24, 24' hold the looped ends of the suture 52 away from the suture introducer head 20 so that the needles 70, 70' pierce the vessel wall 22 and capture the looped ends of the suture 52 outside the perimeter of the suture introducer head 20. Mechanical limits prevent additional movement of the needle trigger 106 once the needles 70, 70' have optimally engaged the suture clasps 56, 56'. Such resistance signals to the physician that the needles 70, 70' have reached an optimal, predetermined location within the suture clasps 56, 56'.

After the physician advances the needles 70, 70' to the optimal, predetermined location within the suture clasps 56, 56', the physician releases pressure on the needle trigger 106, thereby allowing the needle biasing spring 154 within the handle portion 100 (see FIGS. 4-6) to retract the needles 70, 70' proximally. This motion causes the needles 70, 70' to withdraw into the needle lumens 60, 60' with the looped ends of the suture 52 attached to the suture catches 72, 72'. The suture catches 72, 72' capture the looped ends of the suture 52 held by the suture clasps 56, 56' and pull the looped ends up through the needle incisions 80, 80' as the needles 70, 70' retract proximally. As the needles 70, 70' pull proximally on the looped ends of the suture 52, tension in the suture 52 causes additional segments of the suture 52 to feed through the hole 46 at the distal end 54 of the suture introducer head 20, into the artery 14 and through the needle incisions 80, 80'. In this embodiment, the physician may regulate the rate of needle movement by controlling the rate of movement of the needle trigger. From the above, it can be seen that the position of the needles is substantially directly proportional with the position of the needle trigger. Accordingly, by sensing the position of the needle trigger, the physician is provided with a reliable indication of needle position at any given time.

In the above-described embodiment, the physician advantageously controls the position of the needles 70, 70' by depressing and releasing the needle trigger 104. The advancement of the needle is achieved by depressing the needle trigger in a controlled manner, while retraction is achieved by allowing the needle spring to retract the needle while the physician regulates the rate of retraction with the needle trigger. Once the needles 70, 70' have been retracted into the needle lumens 60, 60', the physician depresses the arm release button 108 (FIG. 3) to release the arm trigger 104. The arm release button urges the corner portion 120 of the arm trigger 104 in a distal direction such that the protrusion 120A is released from the first follower member 140, thereby allowing the arm trigger 104 to spring back upward.

Once the arm trigger 104 is released, the arm biasing spring 144 pushes the first follower member 140 distally, thereby moving the actuating rod 58 distally. This relieves the forces applied to the suture arms 24, 24' by the proximal inside edges 78, 78', allowing the suture arms 24, 24' to assume a relaxed state as illustrated in FIG. 14. Upon further distal movement of the first follower member 140, the suture arms 24, 24' move distally until contacting the deflection surfaces 67, 67'. Together with the deflection surfaces 67, 67', the downward force of the actuating rod 58 causes the suture arms 24, 24' to retract into the recessed state within the suture introducer head 20, as shown in FIG. 13. In the recessed state, the suture arms 24, 24' are substantially parallel with the hollow elongate body 32, and the exterior surfaces of the suture arms 24, 24' are substantially flush with the exterior surface of the introducer head 20. This reduces the likelihood that the suture arms 24, 24' will snag or catch on the vessel wall 22 or the flesh 18 during withdrawal. With the suture arms 24, 24' and the needles 70, 70' returned to the recessed state, the device 6 is ready for removal from the artery 14.

With reference again to FIG. 1, the physician then withdraws the device 6 out of the artery 14 and out of the tissue 18 of the patient's thigh 12. After the device 6 is fully withdrawn (and with the CSI 8 still in the tissue 18), the physician gently pulls the ends of the suture 52 to close the vessel incision 16. In the embodiment wherein the suture 52 passes through the needle incisions 80, 80', when the ends of the suture 52 are pulled, tension in the suture 52 closes the vessel incision 16. The physician then ties at least one knot, preferably a fisherman's knot or an improved clinch knot, with the ends of the suture 52 and slides or pushes the knot(s) down through the CSI 8 to the vessel incision 16. The physician may tie and push the knot(s) by using any suitable suture knot tying and/or cinching apparatus including an apparatus disclosed in Applicant's application entitled METHOD AND APPARATUS FOR TYING SUTURE KNOTS, Ser. No. 09/923,108, filed Aug. 6, 2001, the entirety of which is hereby incorporated by reference. Alternatively, the physician may tie at least one knot by hand and then cinch the knot by using a knot cinching device, such as an apparatus taught by Applicant's application titled KNOT PUSHER, Ser. No. 09/571,759, filed May 15, 2000, which is incorporated herein by reference in its entirety. Still, the physician may choose to fasten a small, circular or flat stainless steel clip (not shown) to the ends of the suture 52 and slide the clip down through the CSI 8 to the vessel incision 16 to close the incision 16. Other embodiments for tying and placing knots are described in Applicant's application entitled HANDLE FOR SUTURING APPARATUS, Ser. No. 60/613,636, filed Sep. 27, 2004, and METHOD AND APPARATUS FOR HOLDING SUTURE ENDS TO FACILITATE TYIING OF KNOTS, Ser. No. 60/683,701, filed May 23, 2005, the entirety of both of which are incorporated by reference. The physician then cuts the unused ends (extra length) of the suture 52 and removes the cut portions. The physician then removes the CSI 8 from the patient's thigh 12.

In one alternative embodiment, the suturing apparatus may be provided with a lumen for slidably receiving a guidewire. In one example, the guidewire lumen may be combined with the bleed back lumen. The guidewire lumen is provided for assisting the physician during insertion of the suturing apparatus into the patient and advancing the device toward the treatment site.

Figure 17:
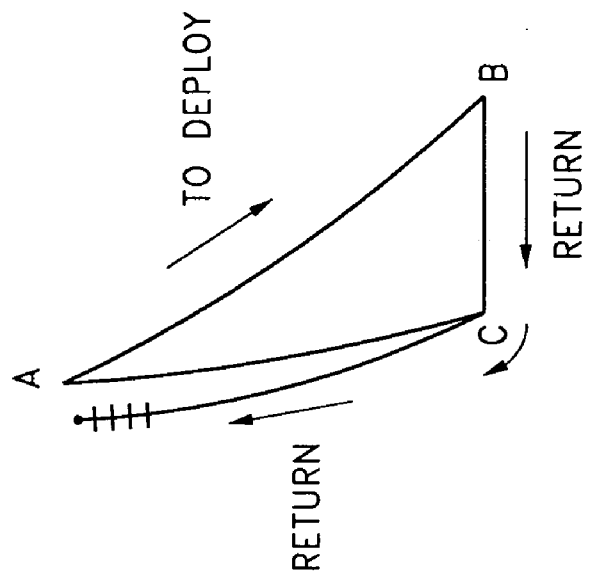
FIG. 17 illustrates an exemplifying path of the camming surface of FIG. 16 during deployment and automatic retraction of the needles.
Figure 16:
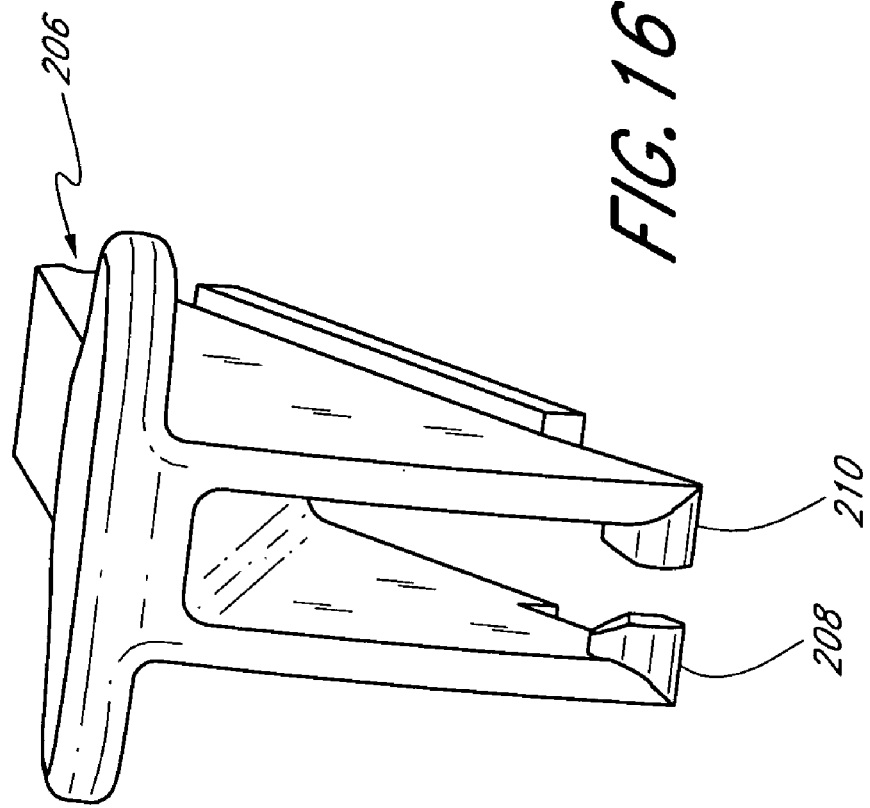
FIG. 16 is a perspective view illustrating an alternative embodiment of a needle trigger wherein the camming surface is provided by a pair of opposing pins with a gap therebetween.
Figure 18:
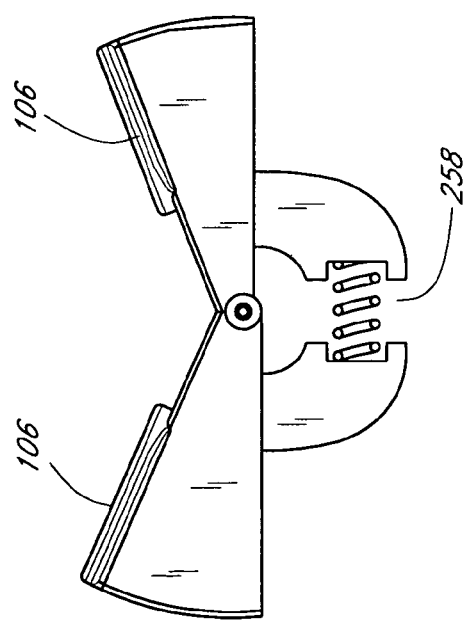
FIG. 18 is a side view illustrating an alternative configuration of the arm trigger and needle trigger wherein a compression spring is provided for biasing the triggers into the non-depressed positions.
Figure 19:
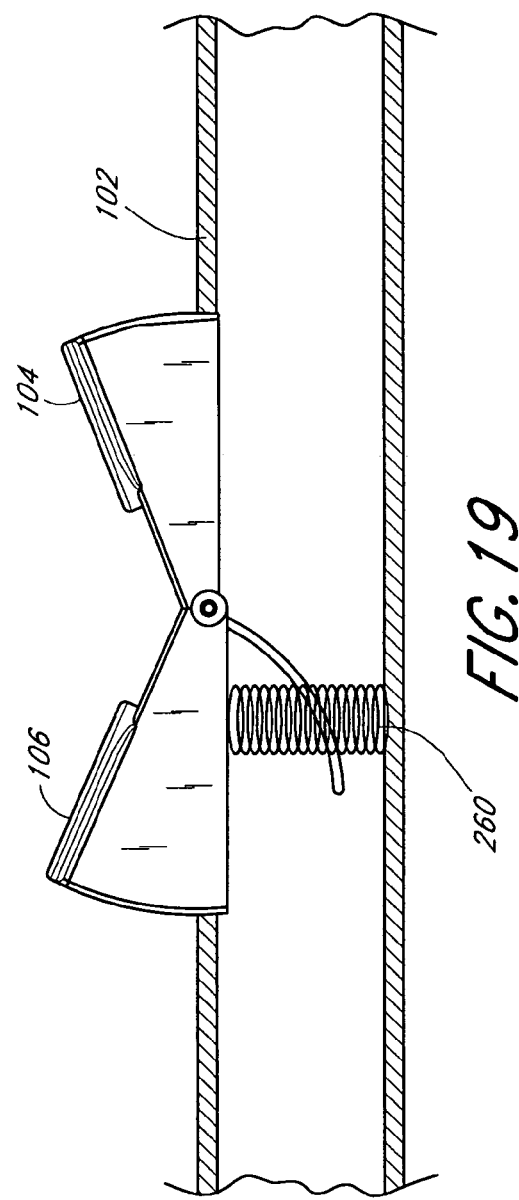
FIG. 19 is a side view illustrating another alternative configuration of the arm trigger and needle trigger having a compression spring in a different location.
Figure 20:
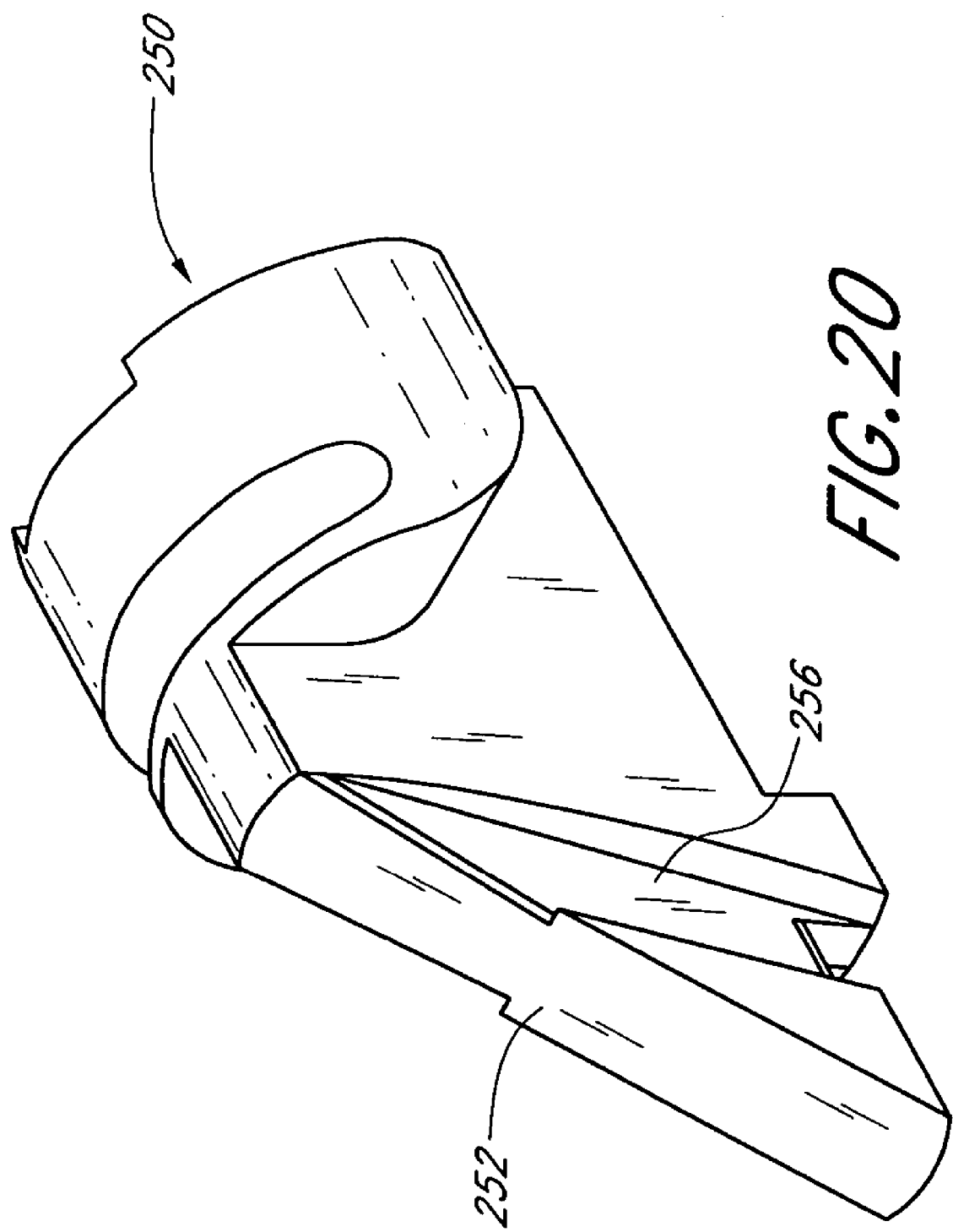
FIG. 20 is a perspective view illustrating an alternative embodiment of a follower member configured for engagement with the needle trigger of FIG. 16, wherein the follower member is provided with an inclined surface and a return slot for guiding the opposing pins back to the starting position.

With reference now to FIGS. 16 through 20, one alternative needle actuation mechanism is provided. With particular reference to FIG. 16, a needle trigger 206 is formed with first and second pins 208, 210 and a gap therebetween. The needle trigger is configured for cooperation with the follower member 250 shown in FIG. 20. In this embodiment, the pins 208, 210 of the needle trigger 206 initially ride along the inclined surface 252 of the follower member 250, thereby causing the follower member to move in a distal direction for extending the needles. However, as the needle trigger reaches a finish (i.e., fully depressed) position, the pins extend beyond the bottom edge of the inclined surface, thereby relieving the force on the follower member and allowing the follower member to snap back in a proximal direction. This occurs while maintaining the needle trigger in the fully depressed condition. Accordingly, the needles are first fully extended and then automatically snap back when the needle trigger reaches a first finished position (i.e., is fully depressed). The needles snap back due to the spring biasing of the follower member. When the needle trigger is released, the pins ride back up via slots 256 to the start position. FIG. 17 illustrates an exemplifying path of the pins during this cycle. FIGS. 18 and 19 illustrate spring mechanism 258 or 260 for biasing the arm and needle triggers back into the start position.

If desired, the relationship between the needle trigger and the follower member may be configured such that the needles retract from the first finished position at a first rate and then retract from a second finished position at a faster rate. This may be achieved by providing a cut away portion (such as in FIG. 9) on the follower member. This retraction of the needles at a slow rate followed by a fast rate advantageously provides a "pre-tensioning" of the suture such that the needles initially tug slowly on the suture ends and then more quickly. The initial slow tugging allows the suture ends to become better aligned before withdrawal through the tissue.

Figure 21:
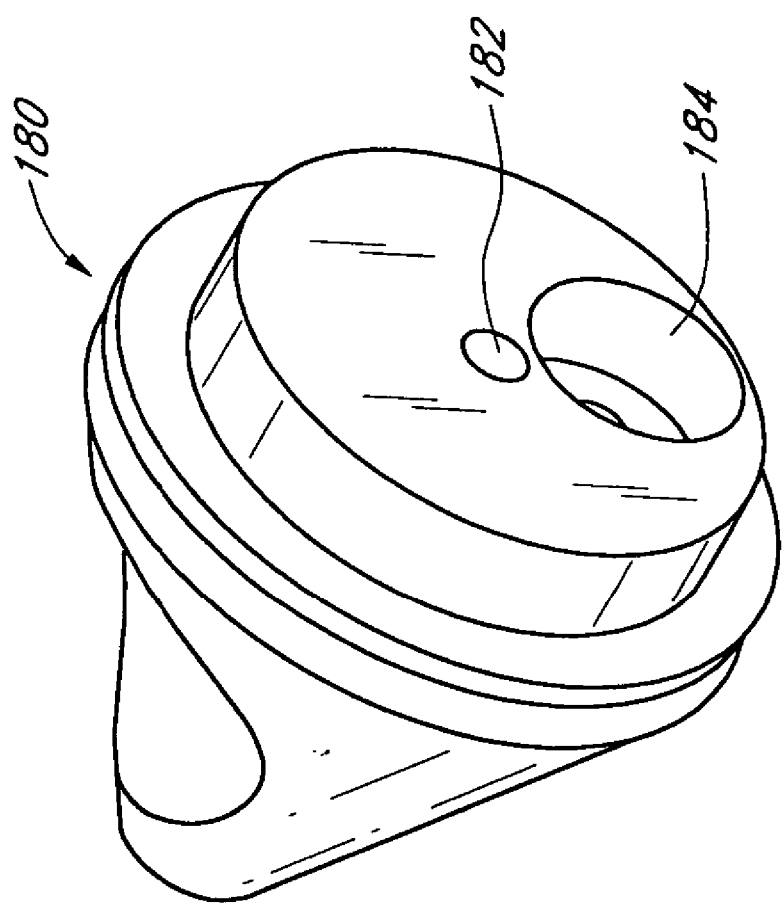
FIG. 21 is a perspective view illustrating one preferred embodiment of an extrusion clamp for securing the elongate body to the handle portion.

With reference now to FIG. 21, one preferred embodiment of an extrusion clamp 180 is illustrated. The clamp provides a transition between the handle portion 100 and the elongate body. The clamp includes a central lumen 182 for receiving the actuator rod and needles. The clamp also includes a depression for seating the needle biasing spring 154.

Figure 22:
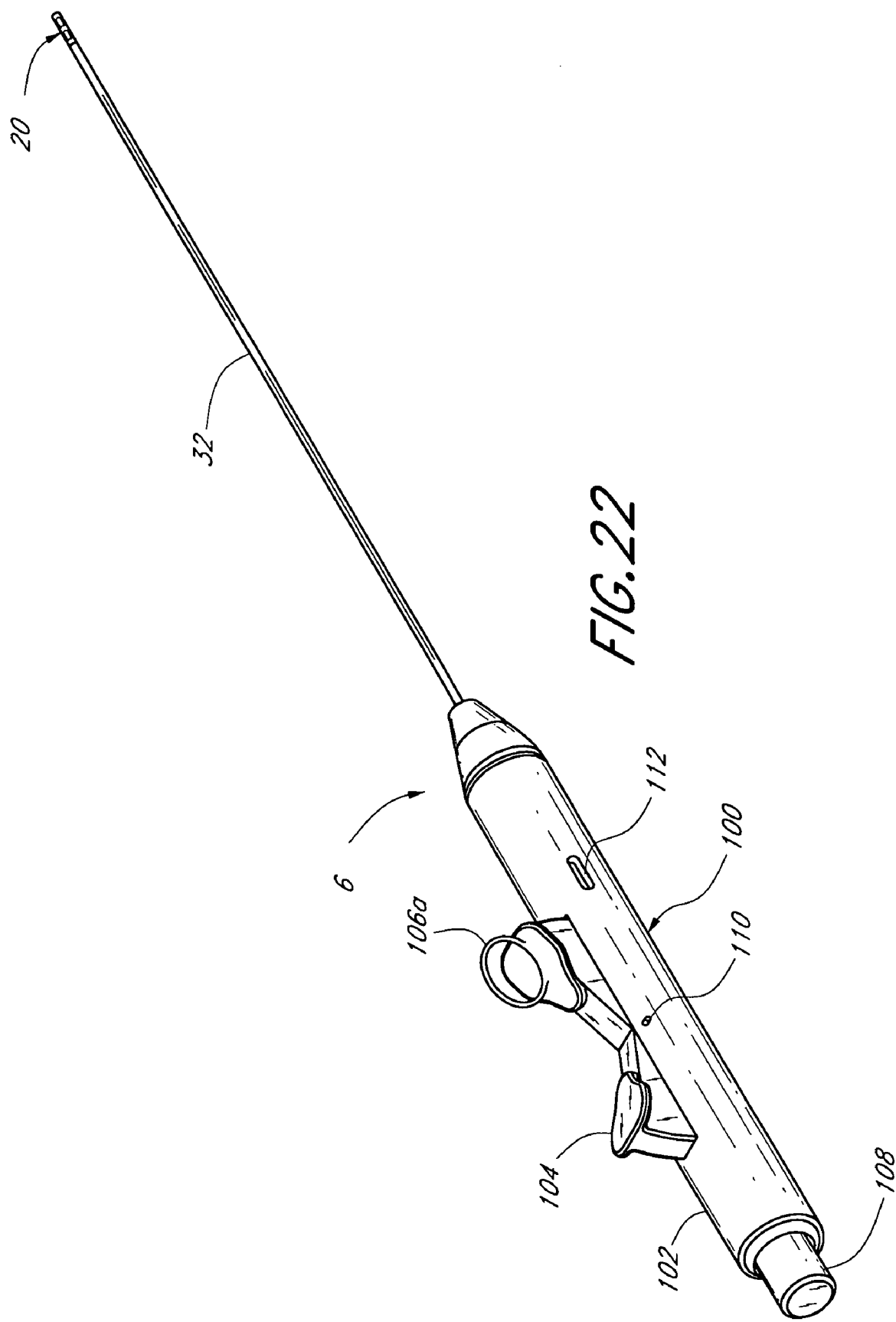
FIG. 22 is a perspective view illustrating an alternative embodiment of a suturing apparatus having an improved handle portion wherein the needle trigger includes a looped portion.

In another alternative embodiment, as shown in FIG. 22, the needle trigger 106A may be provided with a looped portion configured to receive the physician's thumb or finger. The looped portion advantageously allows the physician to pull upward on the needle trigger without relying on the biasing spring force to raise the needle trigger. This embodiment provides the physician with greater control over the movement of the needles.

In another alternative embodiment, the suturing apparatus may be provided without an arm release button. Rather, the arm trigger could be constructed such that the initial depression moves the arm trigger into the locked position. Pressing the arm trigger again causes the arm trigger to become released and pop back up. Any release mechanism of the types known in the art may be used for this purpose.

In another alternative embodiment, it is contemplated that first and second thumb wheels may be provided along the handle portion for moving the first and second follower members. The interaction between the thumb wheels and the follower members preferably employs a rack and pinion system of the type known in the art. This embodiment provides the physician with even greater control over the position of the suture arms and needles.

FIGS. 23-27 illustrate an alternative embodiment of a suturing apparatus 300, wherein the release button 108 is provided along the side, rather than extending axially from [at] the proximal end, of the main housing 102. The suturing apparatus 300 generally comprises an elongate body 32 and an introducer head 20 as described above, and a handle portion 100' as described further below.

Figure 23:
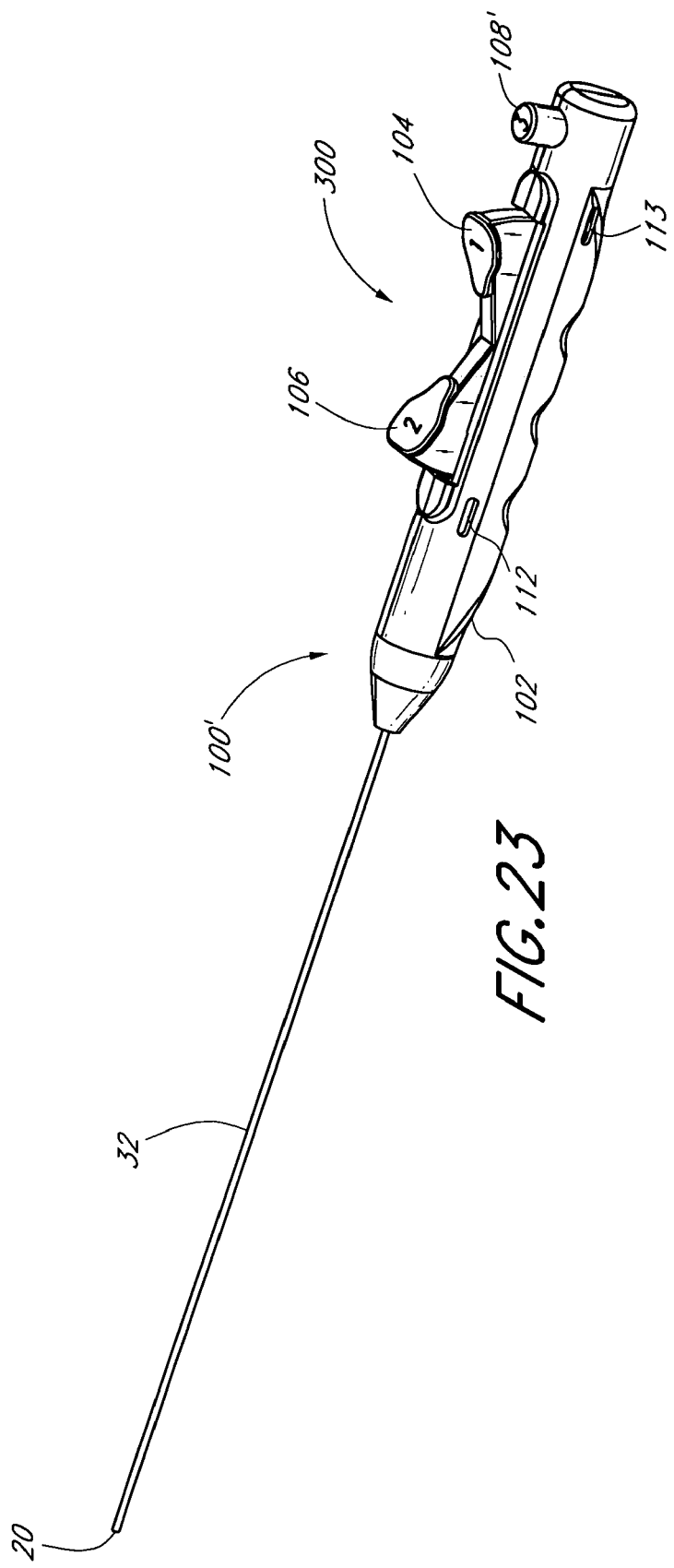
FIG. 23 is a perspective view illustrating another embodiment of a suturing apparatus.

As shown in FIG. 23, the handle portion 100' comprises a main housing 102, an arm trigger 104 and a needle trigger 106 as described above, and an arm release button 108'. The arm trigger, needle trigger and arm release button 108' preferably include markings to indicate the order in which the triggers are actuated, e.g., the arm trigger 104 is labeled "1," the needle trigger 106 is labeled "2," and the arm release button 108' is labeled "3."

Figure 24:
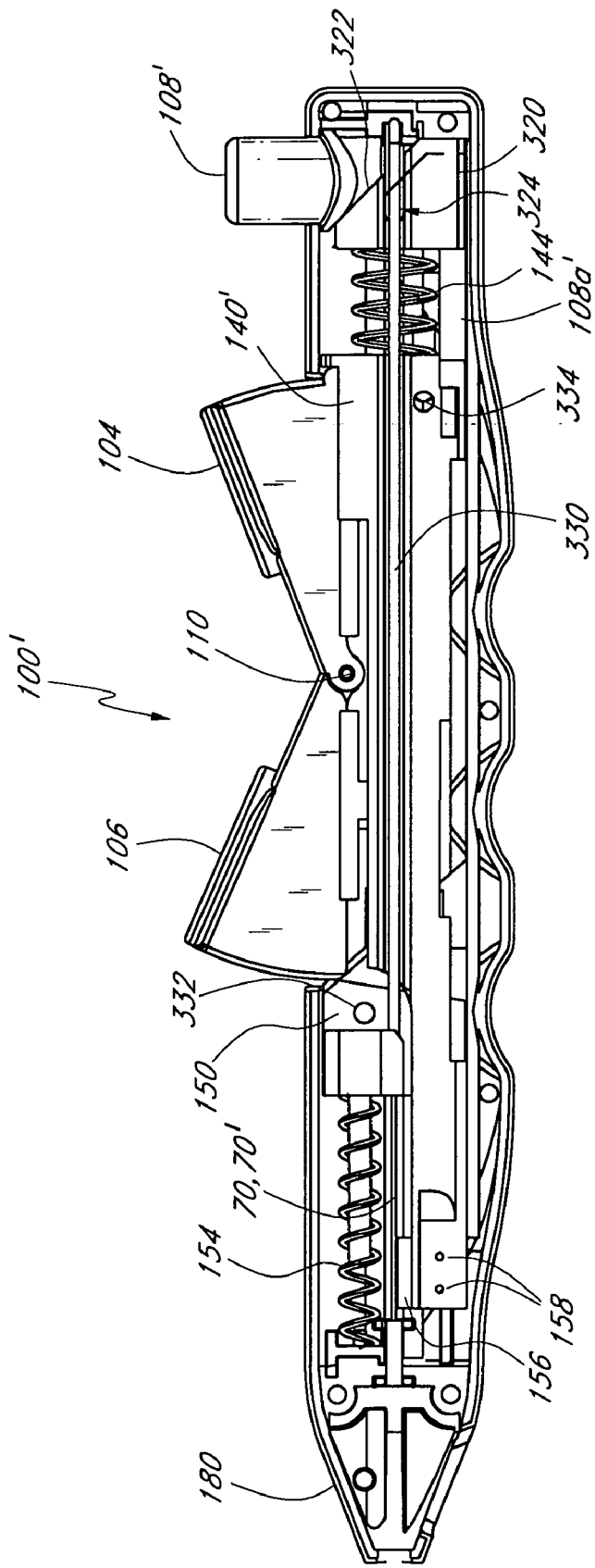
FIG. 24 is a side view of the handle of the suturing apparatus of FIG. 23, with a portion of a housing of the handle removed.
Figure 25:
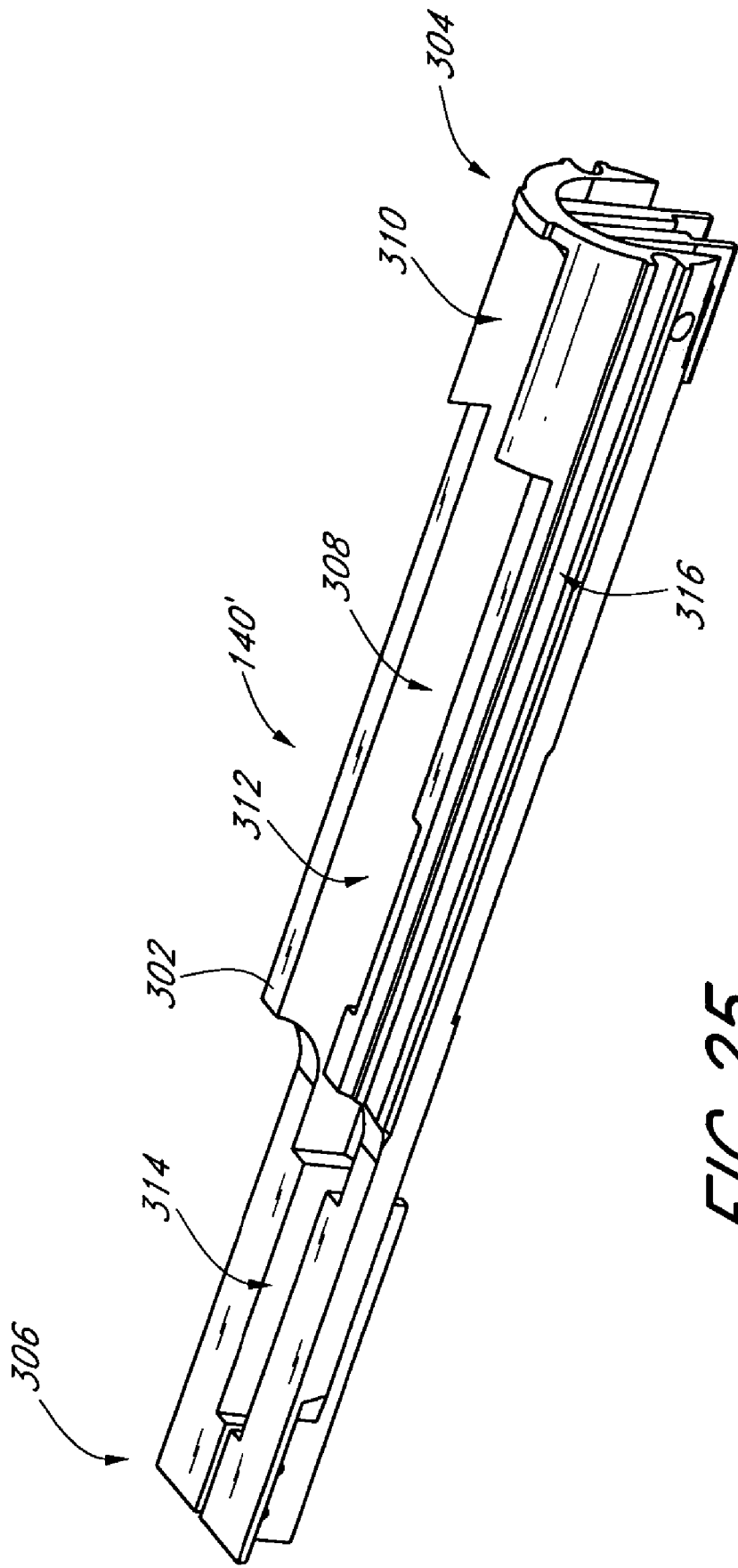
FIG. 25 is a perspective view of the first follower removed from the housing of FIG. 24.

As shown in FIG. 24, the arm and needle triggers are preferably pivotally coupled to the main housing 102 about pin 110 such that the triggers rotate as they are depressed by the physician. When the arm needle trigger 104 is depressed, it engages a first follower member 140' that is slidably received in the main housing 102. The first follower member 140', shown more particularly in FIGS. 25 and 26, comprises an elongate body 302 having a proximal end 304 and a distal end 306 with a slot 308 extending longitudinally through the elongate body along a top side thereof. At the proximal end 304, the elongate body 302 has a partially circular cross-section, with a proximal portion 310 of the slot receiving the arm trigger 104 when depressed. In an intermediate portion of the elongate body 302, an intermediate portion 312 of the slot is provided that partially receives the needle trigger 106 when depressed. In a distal portion of the elongate body 302, a distal portion 314 of the slot is provided that partially receives the needle trigger 106 when depressed, and also receives the second follower member 150, as described further below.

Along both sides of the elongate body adjacent the slot portions 312 and 310, longitudinal grooves 316 are provided to receive an arm lockout wire 330, described further below. An inclined ramp 142' such as described above is provided within the portion 310 of the slot to engage the arm trigger 104.

A drive wire tab 156 as illustrated also in the embodiments above is preferably secured to the distal end of the first follower member 140', such as by pins through holes 158. The tab 156 is secured to the actuating rod 58, which extends through the central lumen 182 of extrusion clamp 180.

Figure 26:
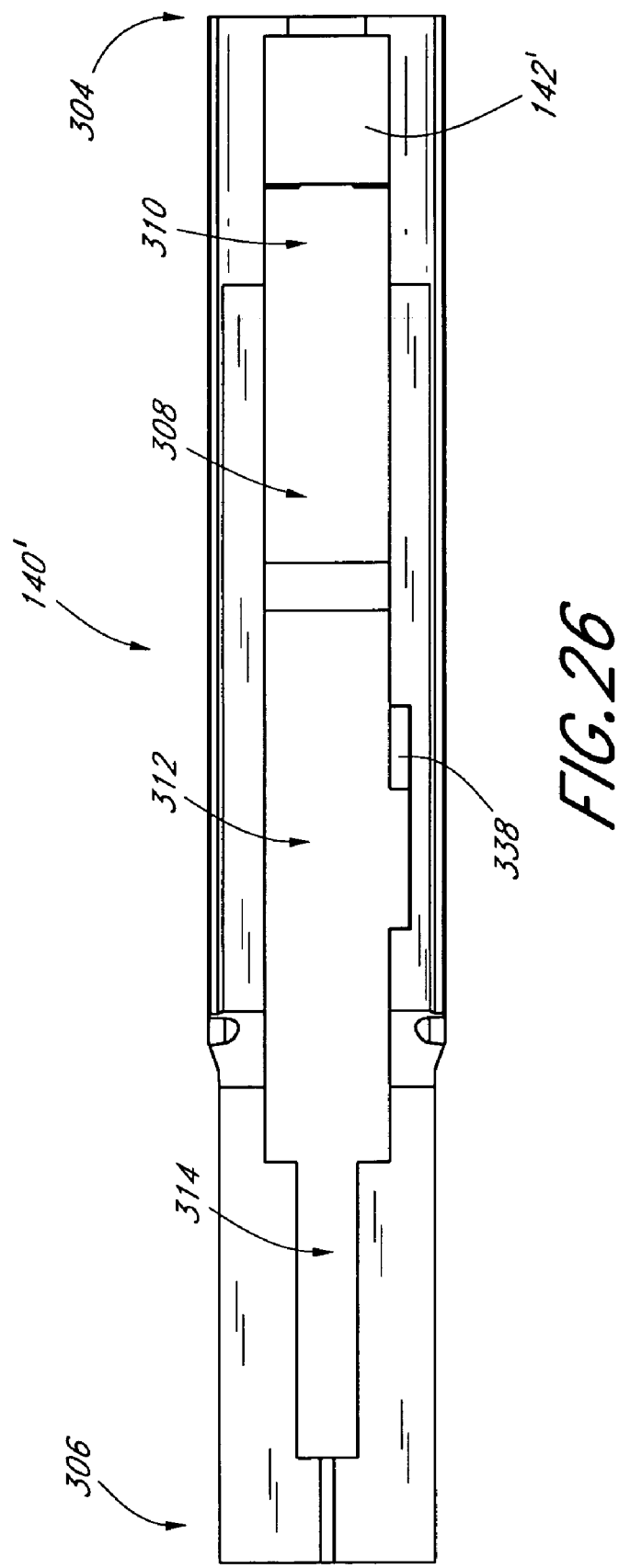
FIG. 26 is a perspective view of the first follower member of FIG. 25 from above.
Figure 27:
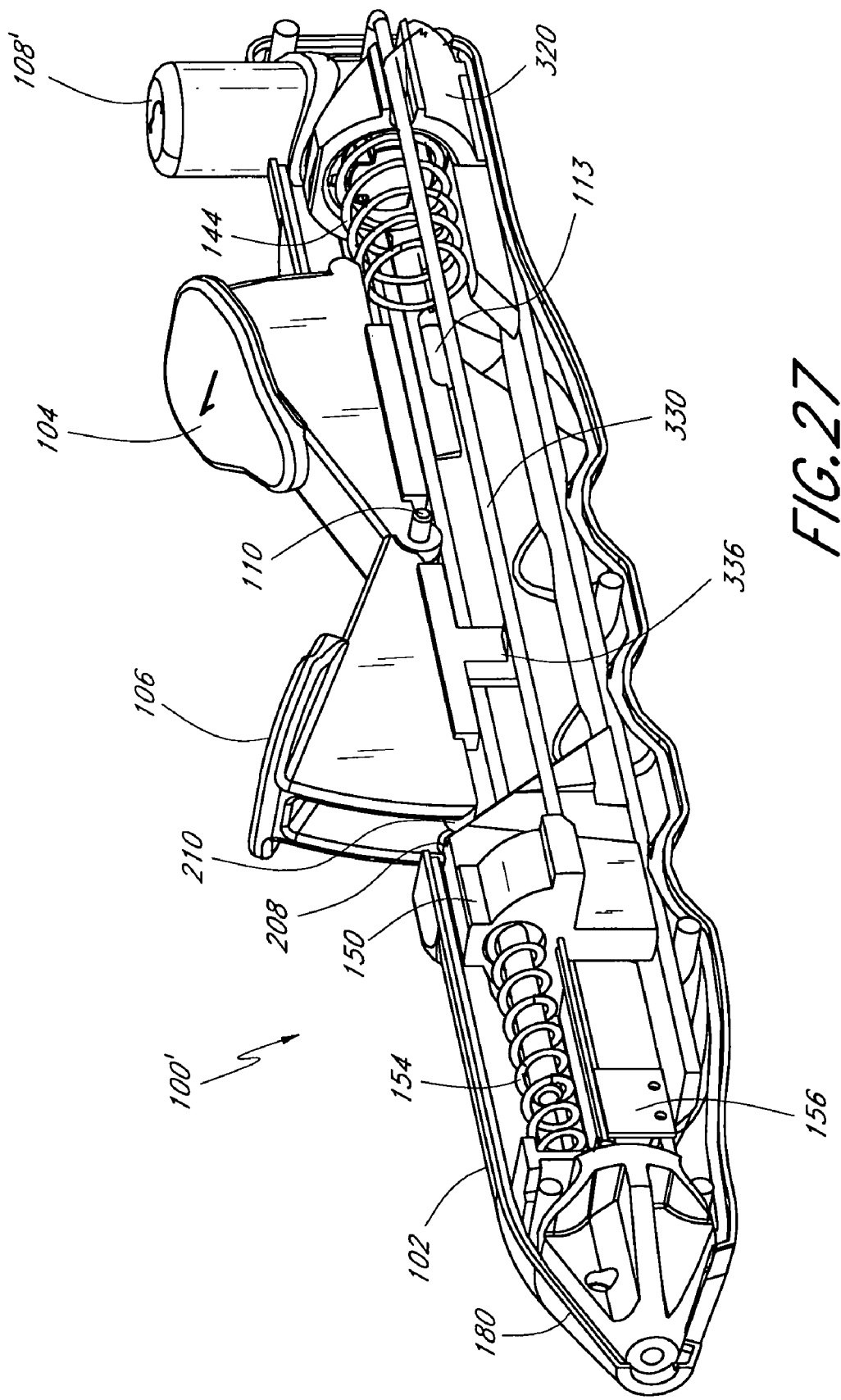
FIG. 27 is a perspective view of the handle of the suturing apparatus of FIG. 23, with the first follower removed.

FIG. 27 illustrates the handle 100' with the first follower member 140' removed. A downwardly extending leg 336 extends from a lower surface of the needle trigger 106. When the first follower member 140' is in its initial configuration, a ledge 338 on the first follower member, shown in FIG. 26, is positioned below the leg 336, preventing the needle trigger 106 from being depressed. When the first follower member 140' is moved proximally, the ledge 338 also moves proximally to allow downward movement of the needle trigger 106. This prevents the needle trigger 106 from being actuated until after the arms are deployed by depressing arm trigger 104.

The needle trigger 106, when depressed, engages a cammed surface 152 of second follower member 150, causing the second follower member 150 to compress needle biasing spring 154, as described above. The second follower member 150 is provided in the distal portion 314 of the slot 308 and is capable of sliding relative to the first follower member. Proximal of the first follower member 140' is an arm spring 144, and proximal of arm spring 144 is third follower member 320, which has an inclined surface 322 which engages arm release button 108'. Third follower member has longitudinal grooves 324 on both sides thereof to receive the arm lockout wire 330 described below. Elongate member 108A' extends distally from the third follower member 320 underneath the arm spring 144.

As shown in FIG. 24, an arm lockout wire 330 extends proximally from the one side of the second follower member 150, through the longitudinal groove 316 on one side of the elongate body 302 of the first follower member 140', through the longitudinal groove 324 on one side of the third follower member 320, around the proximal end of the third follower member, and back through the grooves 324 and 316 on the opposite side of the housing and connecting with the second follower member 150. When second follower member 150 moves distally, arm lockout wire 330 also moves distally, and becomes positioned underneath the arm release button 108'. This prevents the arm release button 108' from being depressed while the needles are being actuated, until the second follower member returns to its initial position.

As shown in FIG. 23, the main housing of the handle portion 100' includes a safety opening or window 112 as described above for manually retracting the needles. The main housing also includes a safety opening or window 113 for manually retracting the arms. The opening 112 cooperates with the opening 332 in second follower member 150, allowing for a pin to be inserted into the openings to manually bring the second follower member back to its initial configuration. The opening 113 cooperates with the opening 334 in the first follower member 140' for the same purpose.

Operation of the suturing assembly 300 as illustrated in FIGS. 23-27 first begins, after appropriate placement of the assembly, by depressing arm trigger 104 labeled "1". Depressing arm trigger 104 causes the first follower member 140' to move proximally within the housing 102, compressing arm spring 144 and moving actuating rod 58 to deploy the arms 24, 24' described above. Arm trigger 104 preferably can be depressed until it is secured or locked in a down position, such as described with the embodiment of FIG. 7 above.

Next, depressing needle trigger 106 labeled "2" causes the second follower member 150 to slide distally within the slot of first follower member 140', compressing the needle biasing spring 154 and causing needles 70 and 70' to splay outward from the elongated body 32. The needle trigger 106 may be configured such as described with respect to FIG. 16 above. More particularly, the needle trigger 106 may have pins 208, 210 that ride initially along an inclined surface of the second follower member 150, thereby causing the follower member to move in a distal direction for extending the needles. As the needle trigger 106 reaches a finish (i.e., fully depressed) position, the pins extend beyond the bottom edge of the inclined surface, thereby relieving the force on the follower member and allowing the follower member to snap back in a proximal direction. This occurs while maintaining the needle trigger in the fully depressed condition. Accordingly, the needles are first fully extended and then automatically snap back when the needle trigger reaches a first finished position (i.e., is fully depressed).

In the embodiment of FIGS. 23-27, the needle trigger may remain in its depressed configuration after the second follower member 150 snaps back to its original configuration, or the needle trigger may automatically return to its initial configuration. If the needle trigger 106 does not automatically return to its initial configuration, the operator may simply pull the needle trigger upward along the body of the second follower member, spreading the gap between the pins 208, 210 until the pins are once again above the inclined surface.

To retract the arms 24, 24', the operator presses down on the arm release button 108', labeled "3". This causes the third follower member 320 to move distally, and causes the elongate member 108A' to contact a corner portion of the arm trigger 104 and urge the arm trigger distally so that it is released from the first follower member 140'.

It should be understood that certain variations and modifications of the above-mentioned methods and apparatus will suggest themselves to one of ordinary skill in the art. The scope of this disclosure is not to be limited by the illustrations or the foregoing description thereof, but rather solely by the appended claims.

What is claimed is:

1. A method of applying suture to an opening, comprising:
    inserting an elongate body into the opening;
    extending at least one arm from the elongate body on a distal side of the opening, the at least one arm holding a suture portion;
    advancing at least one needle from the elongate body from the proximal side of the opening, through tissue adjacent the opening, and into engagement with the suture portion held by the at least one arm; and
    retracting the at least one needle in a distal to proximal direction, pulling the suture portion proximally through the opening;
    wherein the needle is advanced by moving an actuator from a first position to a second position and is biased to retract to its first position, and wherein the at least one needle automatically retracts once the actuator reaches the second position such that the steps of advancing and retracting the at least one needle are both performed as the actuator moves from the first position to the second position.

2. The method of claim 1, wherein the actuator is depressed to advance the needle.

3. The method of claim 1, further comprising returning the actuator to the first position upon release of the actuator after advancing and retracting the at least one needle.

4. The method of claim 1, wherein the needle is spring biased to return to its first position.

5. A method of applying suture to an opening, comprising:
    inserting an elongate body into the opening, the elongate body being connected to a handle having a plurality of actuators;
    depressing a first actuator to extend at least one arm from a first position to a second position, the arm in its second position extending from the elongate body on a distal side of the opening, the at least one arm holding a suture portion;
    depressing a second actuator from a first position to a second position to advance at least one needle from the elongate body from the proximal side of the opening, through tissue adjacent the opening, and into engagement with the suture portion held by the at least one arm;
    continuing to depress the second actuator beyond the second position to retract the at least one needle in a distal to proximal direction, pulling the suture portion proximally through the opening; and
    retracting the arm to its first position.

6. The method of claim 5, further comprising depressing a third actuator to return the at least one arm from its second position to its first position.

7. The method of claim 5, wherein the needle is spring biased to return to its initial position.

8. A method of advancing a needle, comprising:
    providing an actuator capable of being depressed;
    providing a follower having an angled surface, the follower being connected with the needle and the angled surface being engageable with a surface of the actuator;
    depressing the actuator along a first path relative to the follower to advance the needle, wherein the distance moved by the needle is proportional to the angle of the angled surface;
    continuing to depress the actuator along the first path until the actuator surface exits the angled surface of the follower; and
    retracting the needle while retracting the follower such that the actuator moves relative to the follower along a second path, the second path being different than the first path.

9. The method of claim 1, wherein advancement of the at least one needle ceases when the actuator reaches the second position.

10. The method of claim 5, further comprising returning the second actuator to the first position after advancing and retracting the at least one needle.

11. The method of claim 10, wherein the at least one needle is connected to the second actuator via a follower member, wherein the second actuator moves along a first surface of the follower member as the needle is advanced in a proximal to distal direction and the second actuator moves along a second surface of the follower member as the needle is retracted in a distal to proximal direction.

12. The method of claim 8, further comprising returning the actuator to an initial position along a third path of the actuator relative to the follower, the third path being different from both the first path and the second path.

13. The method of claim 8, wherein the second path is defined by retraction of the follower while maintaining depression of the actuator.

* * * * *